United States Patent [19]

Harandi et al.

[11] Patent Number: 4,855,524
[45] Date of Patent: Aug. 8, 1989

[54] PROCESS FOR COMBINING THE OPERATION OF OLIGOMERIZATION REACTORS CONTAINING A ZEOLITE OLIGOMERIZATION CATALYST

[75] Inventors: Mohsen N. Harandi, Lawrenceville; Hartley Owen, Belle Mead, both of NJ.

[73] Assignee: Mobil Oil Corporation, New York, N.Y.

[21] Appl. No.: 250,660

[22] Filed: Sep. 29, 1988

Related U.S. Application Data

[63] Continuation-in-part of Ser. No. 118,926, Nov. 10, 1987, Pat. No. 4,777,316.

[51] Int. Cl.$^4$ .............................................. C07C 2/02
[52] U.S. Cl. ..................................... 585/517; 385/533; 385/716; 385/722
[58] Field of Search ................ 585/517, 533, 716, 722

[56] References Cited

U.S. PATENT DOCUMENTS

| | | | |
|---|---|---|---|
| 3,845,150 | 10/1974 | Yan et al. | 208/135 |
| 3,960,978 | 6/1976 | Givens et al. | 585/531 |
| 4,090,949 | 5/1978 | Owen et al. | 208/78 |
| 4,417,086 | 11/1983 | Miller | 585/530 |
| 4,423,268 | 12/1983 | Miller | 585/533 |
| 4,456,779 | 6/1984 | Owen et al. | 585/415 |
| 4,542,247 | 9/1985 | Chang et al. | 585/254 |
| 4,605,807 | 8/1986 | Mazurek | 585/517 |

FOREIGN PATENT DOCUMENTS

85/05102 11/1985 European Pat. Off.

*Primary Examiner*—Curtis R. Davis
*Attorney, Agent, or Firm*—Alexander J. McKillop; Charles J. Speciale; L. G. Wise

[57] ABSTRACT

A process is disclosed for combining the operation of (i) a primary reactor (referred to as a "MOG" reactor), in which an olefin-containing light gas or light naphtha is oligomerized to gasoline range hydrocarbons, and, (ii) a high pressure secondary reactor (referred to as a "MODL" reactor), to make distillate or lubes, using the effluent (primary effluent) from the MOG reactor as feed for the MODL reactor. In the distillate mode, the primary effluent is tailored so as to be substantially free (less than 3 mol %) of $C_{10}{}^+$ components. Because the $C_{10}{}^+$ "make" from the MOG reactor is spared passage through the MODL reactor, conversion of the $C_{10}{}^+$ components typically experienced due to cracking and oligomerization in the MODL is avoided. Because the $C_4{}^-$ light components which are highly paraffinic, are separated from the primary effluent in a debutanizer to provide a mainly $C_5$-$C_9$ stream, conversion of olefins to distillate in the MODL reactor is enhanced relative to using a feed, not tailored as described, to the MODL reactor. The yield of desired $C_{10}{}^+$ product is surprisingly high. In addition, the throughput to the MODL reactor is substantially reduced. Various embodiments of the process are disclosed to provide economic processes to meet the challenge of oligomerizing lower olefins to distillate and lubes.

30 Claims, 5 Drawing Sheets

PROCESS FOR COMBINING THE OPERATION OF OLIGOMERIZATION REACTORS CONTAINING A ZEOLITE OLIGOMERIZATION CATALYST

This application is a continuation-in-part of application Ser. No. 118,926 filed Nov. 10, 1987 now U.S. Pat. No. 4,777,316 which teaches a semicontinuous multistage process for upgrading olefinic light gas feedstock (termed "light gas" for brevity herein) containing $C_2$–$C_5$ lower, particularly $C_3$–$C_5$, olefins (alkenes) and paraffins (alkanes).

BACKGROUND OF THE INVENTION

This invention relates to a two-stage process, the first stage of which comprises upgrading either light gas, FCC gas, and/or, light naphtha, boiling range 175° C. (347° F.) to 240° C. (464° F.), either of which contains at least 10 percent by weight (% by wt) olefins, to intermediate range hydrocarbons boiling in the range from 50° C. to 204° C. (125° F.–400° F.) ("gasoline") in a primary reactor termed a MOG (for "Mobil Olefin to Gasoline") reactor.

The MOG primary reactor may be operated as either a moving bed, fixed, riser type or fluid bed, the last being the embodiment in which it is preferably operated, for economic reasons. This MOG primary reactor is operated at relatively low weight hourly space velocity ("WHSV", it being understood that WHSV signifies pounds of olefins fed per pound of zeolite per hour) but otherwise under process conditions generally within the ranges specified for those used in a process described in our aforesaid copending '926 application, except that we now operate the MOG reactor to produce higher conversion to gasoline, and at least 1 part distillate for 10 parts gasoline, in an effluent substantially free of aromatics (that is, less than about 3 mol percent), which effluent now contains slightly more paraffins than in our '926 process. Further, the effluent in this invention is condensed and fractionated under conditions different from those in our '926 process so that we now avoid sending $C_{10}+$ ($C_{10}$ and heavier) components to the secondary reactor thus providing a tailored, olefin-rich $C_5+$ feed, substantially free of distillate, to a secondary reactor in which the feed is converted either to distillate, or to lubes depending upon the particular preselected mode in which the secondary reactor is operated.

"Distillate" refers to hydrocarbons boiling in the range from 130° C. to 343° C. (266° F.–650° F.); "lubes" refers to hydrocarbons boiling above 343° C. (650° F.). The secondary reactor is termed a MODL (for "Mobil Olefin to Distillate and/or Lubes") reactor, and is referred to as such (i.e. "MODL") when reference is made to its operation either to make, predominantly distillate (distillate mode operation), or to make, predominantly lubes (lube mode operation). When the secondary reactor is specifically being used to make a major proportion by wt of distillate it will be referred to herein as a "MOD" reactor operating in a distillate mode; and, when this reactor is specifically used to make a major proportion by wt of lubes it will be referred to as a "MOL" reactor operating in a lubes mode. The MODL reactor may, under certain circumstances, also be operated to produce an effluent ("MODL effluent") which contains a larger proportion by wt of gasoline than is present when the reactor is operated in the distillate mode. Under such operating conditions the reactor is referred to as a "MOGD" (for "Mobil Olefin to Gasoline & Distillate") reactor.

The specific embodiments of this invention derive from operating the MOG for maximum conversion to gasoline, which operation also produces a specified minimum fraction of distillate. Tailoring the MOG effluent results in a surprisingly effective combination of conventional unit operations which permit either semi-continuous operation of our process using a single fixed bed MODL reactor; or, continuous operation, whether with plural fixed beds, or a single fluid bed MODL reactor. In this "maximum conversion" operation of the MOG reactor, an exceptionally high conversion of light gas (or, FCC gas), or light naphtha to olefins is obtained at below about WHSV=10 hr$^{-1}$. The relatively high proportion of distillate formed allows recovery of a significant amount of distillate upstream of the MODL reactor and to tailor the MOG effluent to provide an olefin-rich $C_5+$ feedstream substantially free of $C_{10}+$ components to the MODL reactor. But for this tailored olefin feedstream we would not have the unexpectedly high oligomerization of olefins in the MODL reactor along with beneficial processing flexibility and savings in the costs of operation.

Though the general operating conditions of pressure and temperature for both the MOG and the MODL reactors have been disclosed in the prior art, the particular operating conditions of the MOG reactor which produce the substantial distillate content in the MOG effluent at maximum conversion to gasoline, were never recognized. Under the circumstances, considerations relating to the desirablity of separating the distillate from the MOG effluent, or the consequences of doing so, never arose. Nor were the particular operating conditions known for operating a MODL reactor with a tailored $C_5$–$C_9$ feed which produces more distillate than gasoline.

As will be explained in greater detail hereinafter, the specific improvements of providing a debutanizer instead of a deethanizer (used in our '926 application), and placing a gasoline/distillate splitter ("G/D splitter") or a high temperature separator ("HTS") before the MOD reactor in the distillate mode, dramatically reduces the flow to the MOD reactor, decreases the heat of reaction the reactor must cope with, and thus further helps obtain the high conversion in the MOD reactor.

Developments in fluid-bed and fixed bed catalytic processes using a wide variety of zeolite catalysts have spurred interest in commercializing the conversion of olefinic feedstocks to $C_5+$ hydrocarbons including gasoline, diesel fuel, lubes, etc. In addition to the discovery that the intrinsic oligomerization reactions are promoted by ZSM-5 type zeolite catalysts, several discoveries relating to implementing the reactions in an apt reactor environment, have contributed to the commercial success of current industrial processes. These are environmentally acceptable processes for utilizing feedstocks containing lower olefins, especially $C_3$–$C_5$ alkenes, though a significant quantity, up to 40% ethylene, along with olefins and paraffins heavier than $C_5$ may also be present. A predominantly olefinic light gas containing more than 50% by wt, and preferably more than 60%, of combined propene and butenes, is a particularly well-suited feed to oligomerization reactors using a ZSM-5 type catalyst.

In our MOG+MODL combination of staged reactors, only the olefins in the light gas are converted to gasoline in the primary stage fluid-bed MOG reactor, operating with a relatively low activity (alpha) catalyst, at WHSV<10 hr$^{-1}$, and moderate pressure and temperature ("low severity" conditions referred to herein as "easy").

When our process operates in the distillate mode, in the first stage, the MOG reactor produces a predominantly olefinic $C_5+$ MOG effluent which is condensed in a high-temperature knock-out drum to provide a "wild" $C_{10}+$ condensate (so termed because it contains a substantial amount of $C_9-$), and the uncondensed $C_9-$ vapors are then debutanized. In the second stage, the bottoms fraction of $C_5+$ liquid gasoline range hydrocarbons from the debutanizer, is converted to distillate in the MOD reactor, under higher pressure than in the primary stage, but also at low severity.

In the lubes mode, predominantly olefinic $C_4+$ MOG effluent is debutanized and the fractionated $C_5+$ gasoline range hydrocarbons are converted to lubes in the MOL reactor (the secondary stage), under higher pressure than in the primary stage, but also at low severity.

The effectiveness of the combination of a fluid-bed MOG reactor upstream of a MODL reactor, preferably a single semicontinuous fixed bed MODL (for economics), derives in part from the discovery that the ZSM-5 type catalyst, used in our continuous regenerative primary-stage process under our "easy" conditions, does not appear to suffer from a sensitivity (poisoning) to basic nitrogen-containing organic compounds such as alkylamines (e.g. diethylamine), or, to oxygenated compounds such as ketones, a proclivity which is characteristic of the catalyst under the process conditions of prior art olefin oligomerization processes, particularly the fixed bed processes operated at high pressure. Such processes require the addition of hydrogen as a preventative antidote. It will be recognized that alkylamines are used in treating light gas streams, and ketones are typically present in Fischer Tropsche-derived light ends streams, both of which streams are particularly well-suited for upgrading by oligomerization. Though our process is not adversely affected by the presence of hydrogen, there is no readily discernible economic incentive for using hydrogen in either the primary-stage or secondary-stage reactors, and we prefer not to do so.

Though the earliest prior art, moderate-pressure processes, for example those disclosed in U.S. Pat. Nos. 3,827,968 and 3,960,978 to Givens et al, used a zeolite catalyst to oligomerize lower olefins under moderate conditions, and produced excellent conversions to distillate range olefins in a fixed bed microreactor, some over-riding problems relating to operating the process economically were not foreseen (see "Conversion of $C_2$–$C_{10}$ Olefins to Higher Olefins Over Synthetic Zeolite ZSM-5" by W. E. Garwood presented at the Symposium on Advances in Zeolite chemistry before the Division of Petroleum Chemistry, Inc., American Chemical Society, Las Vegas Meeting Mar. 28–Apr. 2, 1962).

The '978 patent discloses that low alpha ZSM-5 and ZSM-11 catalysts not only have reduced activity for cracking n-hexane and other paraffins, but also produce less than 10% by wt aromatics. The runs were made in a fixed bed microreactor, and, at that time, it was not known that the process required the addition of hydrogen to control coke deposition and to prevent poisoning of the catalyst by nitrogen-containing organic impurities. The basic knowledge that low activity ZSM-5 and ZSM-11 type catalysts effectively oligomerized lower olefins, was used to arrive at improvements in "Catalytic Conversion of Olefins to Higher Hydrocarbons" in U.S. Pat. No. 4,456,779 to Owen et al. which discloses oligomerization of olefins in a MOD reactor system of three downflow fixed beds, in series, with intercoolers; and, more recently, in "Conversion of LPG Hydrocarbons to Distillate Fuels or Lubes Using Integration of LPG Dehydrogenation and MOGDL" in U.S. Pat. No. 4,542,247 to Chang et al which discloses fixed beds in a two-stage catalytic process for converting paraffins to olefins which in turn are converted to gasoline and distillate. The first stage reactor is operated under conditions given in U.S. Pat. Nos. 3,960,978 and 4,211,640 to Givens et al. Under these conditions there is a substantial make of aromatics which are undesirable if the effluent from the MOG is to be converted to distillate (aromatics lower the cetane number, among other things).

In the '779 process, multiple fixed bed reactors are used, each operating in the same range of process conditions, and it was essential to dilute the feed to the reactors with both lower alkanes and recycled gasoline, to maintain a controllable exotherm in the bed. To provide the gasoline recycle, the effluent from the operating reactors (a spare reactor is always being regenerated) is debutanized after oligomerization of olefins is completed. Moreover, the fixed-bed processes in both the '247 and '779 patents require the addition of hydrogen for the reasons given hereinabove. Thus, despite operation at as high a pressure as is economically feasible, the use of hydrogen with a high concentration of lower alkanes dictates that the oligomerization be carried out in the gaseous phase, or vapor/liquid phases, thus aggravating both the heat transfer and mass transfer problems. When we use one or more fixed bed MODL reactors, they may operate with the hydrocarbons in the liquid, gas or super-dense phase, the conditions of operation, irrespective of the phase in which the reactor operates, being determined by economics. When we use a fluid bed MODL reactor, it operates in the super-dense phase, as will be explained in greater detail hereinafter.

Because Chang et al first dehydrogenated a paraffinic feed, they typically converted 30–40% of the paraffins to olefins. The feed to the MOG reactor therefore was predominantly $C_3/C_4$ paraffinic, as was the effluent from the MOG reactor, since the undehydrogenated $C_3/C_4$ paraffins are not oligomerized. Because, after oligomerization in the '247 fixed bed MOG reactor, the effluent still contained a major proportion of $C_3/C_4$ paraffins, Chang et al had to separate the paraffins from the olefins in the effluent (so that the separated $C_4-$ paraffins could be recycled to be dehydrogenated). Since, under their conditions, the make of $C_{10}+$ components was relatively small, they failed to realize the criticality of separating the $C_{10}+$ components before the effluent from the MOG reactor was further oligomerized.

Though neither Owen et al, nor Chang et al, knew it at the time, in practice, a fixed bed requires the addition of a substantial quantity of hydrogen (for the reasons given), which fixed bed nevertheless is far less effective than a fluid bed for the specific purpose of "cleaning up" the MOG effluent. It is this volume of hydrogen which adds to the already large volume of diluents being used as a heat sink, albeit an inefficient one. Nothing in either the '779 or the '247 patents suggests the surprising benefits of operating with a fluid bed in the absence of added hydrogen and fluidized with a feed containing too little alkanes to serve as a significant heat sink, namely less than about 50% by wt, preferably less than 30% by wt.

The earlier references disclosed that the product distribution from an MOGD reactor may be tailored by controlling process conditions, such as temperature, pressure and space velocity. Gasoline ($C_5$–$C_{10}$) is readily formed at elevated temperature (preferably about 400° C.) and pressure from ambient to about 2900 kPa (420 psia), preferably about 250 to 1450 kPa (36 to 210 psia). Olefinic gasoline could be produced in good yield and may be recovered as a product; or, it could be fed to a low severity, high pressure reactor system for further conversion to heavier distillate-range products. Distillate mode operation could be employed to maximize production of $C_9+$ aliphatics by reacting the lower and intermediate olefins at high pressure and moderate temperature. Operating details for typical MOGD oligomerization units are disclosed in U.S. Pat. Nos. 4,456,779 and 4,497,968 (Owen et al); 4,433,185 (Tabak); 4,456,781 to Marsh et al; and U.S. patent application Ser. No. 006,407 to Avidan et al.

None of the foregoing alternatives disclosed the technical and economic difficulties of operating the MODL reactor with a significant proportion of a $C_4-$ fraction in the feed, coupled with the advantages of feeding a tailored $C_5$–$C_9$ olefinic stream to a MODL reactor. Therefore they failed to suggest using them in combination with processing steps made possible with strategically positioned unit operations, namely the use of a knock-out drum, debutanizer (or depentanizer) and G/D splitter, to provide such a stream; nor does any combination of processing steps in the prior art suggest the benefits which enure to a person using our process.

The combination of a relatively low pressure fluid-bed, primary MOG reactor and, a higher pressure secondary MODL reactor is unexpectedly effective because the fluid-bed primary stage rids the feed of poisons while operating under "easy" conditions which produce the maximum conversion of olefins to $C_5+$ olefins, substantially free of aromatics, economically. Since only the gasoline is to be fed to a fixed or fluid bed MODL reactor, after separation of the "light ends", namely $C_3-$ or $C_4-$ components (depropanizing or debutanizing) which may still contain poisons not adsorbed by the catalyst, the benefits of recycling the light ends or incompletely converted olefins, is great compared with the disadvantages of operating the MOG reactor for maximum conversion to gasoline under higher severity conditions. Because the distillate formed in the MOG reactor bypasses the MODL reactor, only gasoline is fed to the MODL reactor, we obtain excellent per pass conversion and selectivity to distillate. Because a substantial portion of the coke formation takes place in the MOG fluid bed, our MODL reactor desirably operates with little coke deposition.

This invention therefore provides either a continuous or semicontinuous process for oligomerizing light gas containing propene, butenes and pentenes, in a MOG reactor, whether fixed, fluid or moving bed, preferably a fluid bed, to produce a substantially $C_4+$ stream in the absence of added hydrogen; separating a $C_5+$-rich fraction from the MOG effluent; and, feeding the $C_5+$-rich fraction to the fixed bed, preferably liquid phase, or fluid bed, preferably super-dense phase MODL reactor. A fixed bed MOG reactor may be used when operating with substantially "clean" or poison-free feed; a moving bed may be used when the disadvantage of dealing with its inherent mechanical problems is outweighed by the advantages of better control of fines. The MODL reactor, whether in the distillate mode or the lubes mode, operates with unexpected efficiency because the gasoline feed is essentially free of inerts and poisons.

U.S. Pat. Nos. 4,417,086 and 4,417,087 to Miller teach a two-zone reactor operating in the transport mode where the relative superficial gas velocity is greater than the terminal velocity in free fall. Though the operation of a fluid-bed is illustrated (example 2 in each of the '086 and '087 patents) note that no operating pressure is stated in the former, and that operating pressure in the latter is 10 psig (24.7 psia, 170 kPa). The general disclosure that the processes may be operated at a pressure in the range from subatmospheric to several hundred atmospheres, but preferably 10 bar or less, and most preferably 0 to 6 bar, (see middle of col 6 in '086, and, near top of col 5 in '087) is not so ingenuous as to be meant to apply equally to the fixed bed (example 1 of '086 and '087, each illustrates 34.5 bar, 500 psi) and the 170 kPa fluid-bed.

In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity. Garwood et al have also contributed to the understanding of catalytic olefin upgrading techniques and have contributed improved processes as in U.S. Pat. Nos. 4,150,062, 4,211,640 and 4,227,992. The '062 patent discloses conversion of olefins to gasoline or distillate in the range from 190°–315° C. and 42–70 atm; and this, and the '640 and '992 disclosures are incorporated by reference thereto as if fully set forth herein.

SUMMARY OF THE INVENTION

We have discovered a process for combining the operation of primary and secondary oligomerization reactors, each containing a crystalline zeolite catalyst, each operating at sufficiently low severity so as to make very little paraffins and essentially no aromatics, while converting a major amount of the olefins fed to each reactor; the primary reactor, a fluid-bed MOG, operates at moderate pressure below 2859 kPa (400 psig) at relatively low WHSV in the range from about 0.1 to about 10 $hr^{-1}$ so that there is a major amount by weight of $C_5+$ ($C_5$ and heavier hydrocarbons) in the MOG effluent in which the pentane to pentene weight ratio is less than 0.2 ($C_5$:$C_5=<0.2:1$), and a minor amount of $C_4-$ hydrocarbons; the second, a fixed bed MODL, optionally, a fluid bed MODL, operates at a higher pressure than the MOG, the MODL reactor also operating in the same range of WHSV as the MOG reactor.

In the distillate mode, this process, unlike our '926 process, avoids sending $C_{10}+$ components to the MODL reactor. Whether in the distillate or lubes mode, our process avoids using an absorber, thus also a lean oil absorbent; and, produces a $C_5$ to $C_9$ olefin-rich feedstream substantially free of $C_4-$ and aromatic components to the MODL reactor. The efficiency of our process derives mainly from this overriding difference in compositions of feedstreams to the MODL reactor.

When the process is operated in either of two distillate modes, the unit operations to which the MOG effluent is subjected, produce a surprisingly high per pass conversion of distillate (hence the term "MOD" reactor for the distillate mode) such that the weight of distillate is greater than that of gasoline produced by the combination of MOG and MOD reactors.

In a first distillate mode, these operations include placing intermediate the reactors, (i) a first fractionator (debutanizer) or other separating means, to provide a $C_5^+$ olefin-rich gasoline feed for the MOD reactor and a $C_4^-$ (butanes, butenes, propane, propene, ethane, and ethene) along with hydrogen, nitrogen, etc. recycle stream for recycling to the MOG reactor, and (ii) a second fractionator or other separating means ("G/D splitter") upstream from the MOD reactor, so that (i) serves to debutanize the MOG effluent, and (ii) serves to remove distillate produced not only in the MOG reactor but also that produced in the MOD reactor. Together, (i) and (ii) provide a tailored feedstream to the MOD reactor which provides the aforesaid per pass overall process conversion and maximizes the yield of distillate from the light gas or light naphtha.

In a second distillate mode, the unit operations include placing intermediate the reactors, (i) a moderate pressure, high temperature, liquid-phase/gas-phase separating means ("high-temp separator", HTS) together with (ii) the debutanizer, and placing downstream of the MOD reactor (iii) the G/D splitter, so that (i) serves to remove distillate and light gases from the effluent of the MOG reactor before the effluent is led to the MOD reactor, and (iii) separates $C_9^-$ ($C_9$ and lighter) components from the desired distillate product.

When the process is operated in the lubes mode, a high, commercially significant, yield of lubes is produced.

The MODL reactor containing a ZSM-5 type of catalyst, may be operated either as a single or multiple fixed bed, or a fluid bed operating in the super-dense phase. The oligomerization in the fixed bed MODL reactor may be effected in the liquid phase; in the fluid bed MODL reactor, oligomerization may proceed in the gaseous phase in the absence of liquid, but preferably, in the super-dense phase at near-critical or super-critical pressure greater than about 2860 kPa (400 psig) at a temperature high enough so that no liquid is present in the fluid bed. In either embodiment, the MODL reactor operates without sacrificing its ability to provide better than 60% selectivity from olefins, to either distillate or lubes.

It is therefore a general object of this invention, to operate first and second (also referred to as primary and secondary) oligomerization reactors, to oligomerize either an olefinic light $C_5$-$C_7$ naphtha or an olefinic $C_2^+$ light gas, for example a LPG feed stock containing from 10-40% by wt $C_2$-$C_5$ olefins, but preferably one containing a major molar proportion of $C_3$-$C_4$ olefins with a minor amount (less than 50%) by wt of $C_2^+$ paraffins, and less than 30 mol % hydrogen, to yield either distillate or lubes, without adding hydrogen in the process.

In either mode, the fluid bed MOG reactor containing a ZSM-5 or "zeolite beta" type of catalyst, operates under "easy "conditions, namely aforesaid low WHSV, relatively low pressure, a superficial vapor velocity of from 0.1 to 1 m/sec (0.3-3 ft/sec), and an outlet temperature below about 400° C. (750° F.), to convert at least 60% by wt, preferably at least 80% by wt, of the $C_3$-$C_4$ olefins in the feedstock to $C_5^+$ olefins at low severity conditions (equilibrated alpha in the range from 1 to 10), but which conditions also produce less than 10% by wt of $C_2^-$ hydrocarbons.

In the first distillate mode the aforesaid unit operations comprise, (a) debutanizing the effluent from the MOG reactor;

(b) feeding the debutanized $C_5^+$ stream to the G/D splitter to separate $C_9^-$ (mainly, gasoline and lighter) components which are to be fed to the MOD reactor;

(c) oligomerizing the separated $C_9^-$ stream in the MOD rector under conditions which provide an effluent containing more distillate than gasoline, (d) flowing the MOD reactor effluent to the G/D splitter and recovering the bottoms from the G/D splitter as distillate product.

Depending upon the composition of the light gas feed, the type and condition of the oligomerization catalyst, the particular process conditions of operation of the MOG reactor, and the economics of operating the specific process set forth immediately hereinabove, an alternative mode of the process may be used. This alternative variation of the process in the second distillate mode comprises, (a) condensing at least a portion of the effluent from the MOG reactor so as to separate a "wild $C_{10}$" (because it contains $C_9^-$ components) portion from the remainder of the gaseous hydrocarbons (mainly $C_9^-$) in a first moderate pressure and high temperature separating ("first HTS") means;

(b) debutanizing the mainly $C_9^-$ hydrocarbons in a debutanizing means ("first debutanizer") to obtain a $C_5^+$ stream;

(c) feeding the $C_5^+$ stream (debutanizer bottoms) to the MOD reactor;

(d) oligomerizing the debutanizer bottoms in the MOD reactor to provide an effluent containing more distillate than gasoline, (e) flowing the MOD reactor effluent and first HTS bottoms to a second HTS or second debutanizer;

(f) mixing the gaseous effluent from either the aforesaid second HTS, or second debutanizer, with the MOG reactor effluent or with the feed to the MOG reactor, and, (g) flowing the distillate-containing liquid stream from either the second HTS (or second debutanizer) to a G/D splitter to recover product distillate as the G/D splitter bottoms.

In either embodiment of the distillate mode, only the essentially distillate-free material is fed to the MOD reactor.

In the lubes mode the aforesaid unit operations comprise, (a) condensing a major portion of the MOG effluent from the MOG reactor and directly debutanizing the unseparated gas and liquid phases of the condensate to provide a $C_5^+$ feedstream, (b) feeding the separated $C_5^+$ feedstream to a MOL reactor; and, (c) recovering the lubes product from the MOL effluent (from the MOL reactor) by separating condensed MOL effluent in a D/L splitter. The gasoline and distillate taken as the overhead of the D/L splitter may be withdrawn as product. A portion may also be recycled to the MOL reactor.

In either the distillate or lubes mode, the MOD or MOL reactor operates under high pressure, moderate temperature, and low WHSV, resulting in maximum conversion to $C_{10}^+$ distillate, or, $C_{20}^+$ lubes, respectively.

It is a specific object of this invention to operate a single fluid-bed MOG reactor containing a ZSM-5 type catalyst, in the gaseous phase, preferably at a pressure in the range above 447 kPa (50 psig) but below 2170 kPa (300 psig), most preferably from about 930 kPa to about 1200 kPa (120-160 psig), and with an olefin partial pressure greater than about 300 kPa (45 psig), to produce an MOG effluent comprising less than 20% by wt $C_4^-$ olefins which are separated from the $C_5^+$ portion, and the $C_5^+$ portion separated from the "wild $C_{10}$" portion, so that substantially only the $C_5$–$C_9$ portion of the effluent from the MOG reactor is flowed to a downstream fixed bed or fluid bed MODL reactor which operates at lower pressure and/or with greater selectivity than it would operate if $C_5^-$ hydrocarbons, inerts and non-oligomerizable, or difficultly oligomerized components were also flowed to it.

It is another specific object of this invention to operate a fluid bed or fixed bed MODL reactor with a tailored gasoline feedstream substantially free not only of inerts, aromatics and $C_5^-$ components, but also of $C_{10}^+$ components, so that the critical pressure at which a liquid phase is formed, is lowered, thus making it possible to operate the MODL reactor at lower pressure. In the fixed bed configuration, the MODL reactor preferably operates with the reactants, intermediates and product in the liquid phase, at a pressure below 7000 kPa (1000 psig), most preferably about 3550 kPa (500 psig) to produce distillate; and, below 13900 kPa (2000 psig), most preferably about 7000 kPa (1000 psig) to produce lubes; and, in a super-dense fluid-bed MODL reactor, solid catalyst particles are fluidized with $C_5$–$C_{10}$ components in the super-dense phase at near-critical or supercritical pressure in the range above about 3200 kPa (450 psig) without forming a liquid phase.

Yet other specific objects of this invention are to combine the operation of MOG and MODL reactors to maximize the production of distillate from a lower olefin-containing light gas, or light naphtha, by removing $C_{10}^+$ distillate made in the MOG reactor before it can be oligomerized to $C_{20}^+$ lubes or less desirable heavy distillate, or thermally cracked to lower olefins in the MODL reactor, because the absence of non-oligomerizable components enhances selectivity and conversion, at the same time permitting operation of the MODL reactor at lower pressure than if such components were present; to minimize the cost of the MODL reactor which is smaller and operates at lower pressure because of the missing, otherwise large volume of $C_4^-$ components; and, to simplify the recovery of the distillate or lubes for better economy, because there are substantially fewer components to separate from the MODL effluent.

BRIEF DESCRIPTION OF THE DRAWING

The foregoing and other objects and advantages of our invention will appear more fully from the following description, made in connection with the accompanying drawings of a preferred embodiment of the invention, wherein.

Figure 1:
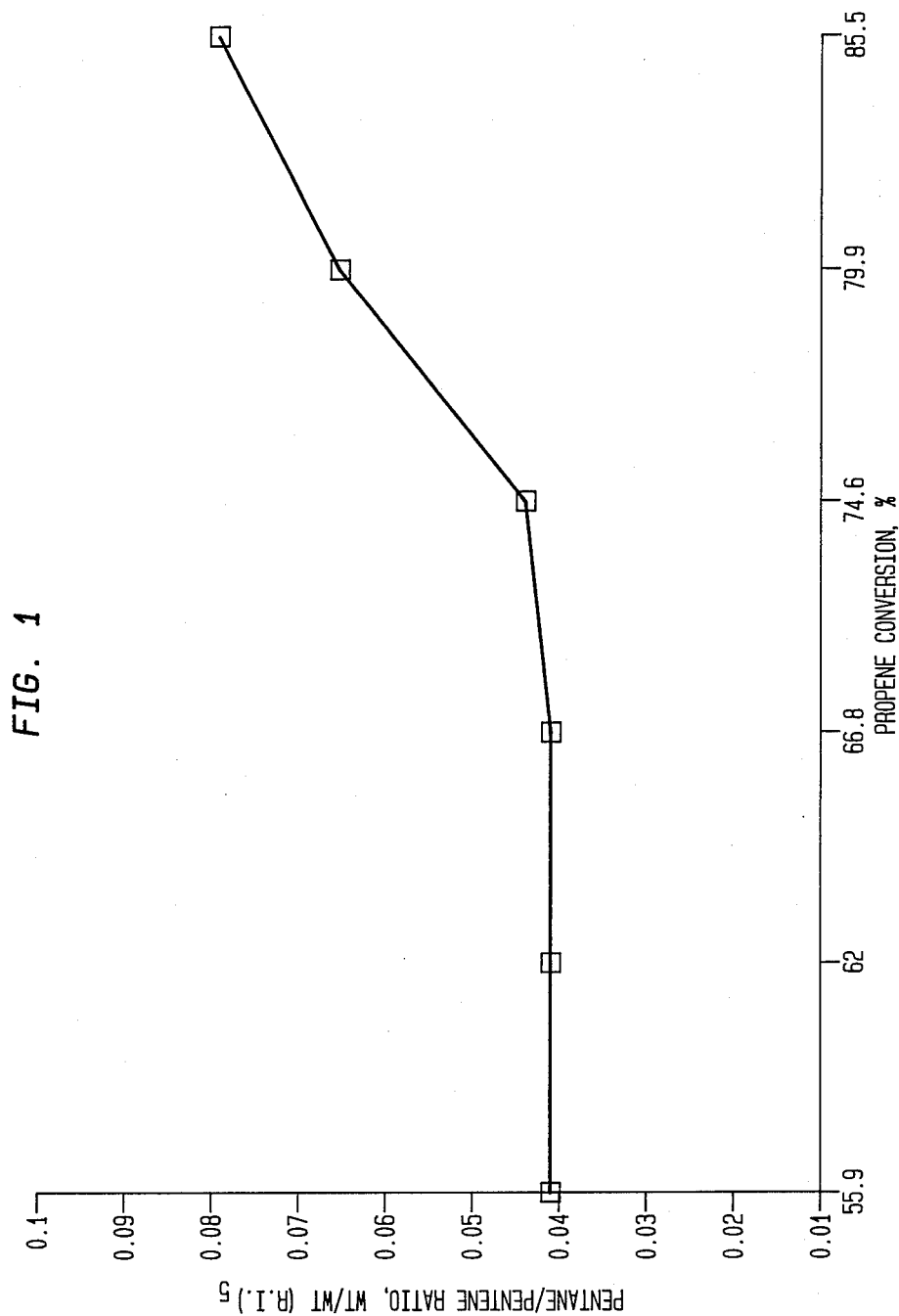
FIG. 1 is a linear plot showing propene conversion vs pentane/pentene ratio, wt/wt in the MOG reactor.

Though the MOD and MOL reactors are each illustrated as single fixed beds (the most preferred embodiment) either or both may also be used in single fluid bed or multiple fixed bed configurations. In the single fixed bed embodiment illustrated, the MOD or MOL reactor is taken off-stream to be regenerated, for economy, and the process is therefore semicontinuous. If desired, a "swing" fixed bed MOD or MOL reactor may be used to avoid semicontinuous operation.

DETAILED DESCRIPTION OF PREFERRED EMBODIMENTS

A typical prior art MOG reactor using a crystalline zeolite, for example as in the Chang et al '247 patent, uses a fixed bed to convert olefins, diluted with a major amount by weight of paraffins, into "heavies" in a single zone operating at the high end of its specified pressure range to maximize the production of gasoline. The fractionated $C_5^+$ MOG effluent contains more than 5% by wt aromatics and generates almost an equal weight of paraffins, all of which, including $C_{10}^+$ components, are fed to a MOD reactor, downstream of the MOG reactor. The MOD reactor in turn operates at a temperature above 260° C. (500° F.) and at the high end of its specified pressure range, to convert the effluent from the MOG reactor into distillate, the reaction proceeding in the gaseous phase. The two reactors are operated in combination, the MOG reactor operating at a lower pressure than the MOD reactor, and the MOD reactor operating as plural fixed beds in series, with the reactants in the liquid phase at a pressure in the range from about 4200 kPa (600 psig) to about 7200 kPa (1000 psig) and a temperature in the range from about 177° C. (350° F.) to about 315° C. (600° F.).

As might be expected, and is well known, the lower alkanes in the light gas are not oligomerized and are therefore deemed "inert". They provide a flowing mass to help control the exotherm, then pass through the MOG essentially unconverted. In the same category as methane and ethane, that is, of inerts, are hydrogen and nitrogen which may be present, or be generated in the MOG reactor. In a typical light gas feed these "inerts" may range from about 10–40% by weight, all of which is a diluent in the heavies effluent from the MOG. This effluent is then cooled and pumped to raise the pressure above 450 psig before it is heated to the desired (MOD feed) temperature and flowed to the MOD. The relatively low partial pressure of the olefinic heavies in the MOD reactor (because of the diluent propane and butanes) adversely affects both the selectivity and the size of the MOD unit. This adverse effect of decreased partial pressure is particularly exaggerated because the volume of the inerts is relatively high compared to that of the olefinic heavies (which, having been oligomerized occupy less volume).

In our novel process we have not only eliminated the problem of decreased partial pressure of the olefinic heavies by eliminating the diluents, but by separating the $C_{10}^+$ fraction before feeding gasoline and associated lower olefins to the MODL reactor, we minimize the feed rate to the the MODL reactor, and avoid the partial conversion of the $C_{10}^+$ fraction it would otherwise suffer. In addition, we produce a substantially poison-free and aromatics-free MOG effluent which is withdrawn from the primary reaction zone containing a major amount by wt of $C_5^+$ hydrocarbons and a minor amount of $C_4^+$ hydrocarbons; and this effluent is tailored to result in exceptionally high per pass conversions and yields of either distillate or lubes in our secondary reaction zone whether it is operated in the fixed bed, liquid-phase or liquid/gas-phase mode, or a fluid bed, super-dense phase mode.

The operation of a fluid-bed MOG reactor under the foregoing maximum conversion conditions which generates essentially no paraffins and no aromatics upstream of the MODL reactor, but at least one part of distillate for every fifteen (15) parts by wt of gasoline range and lighter hydrocarbons ($C_{10}^+:C_9^- > 1:15$), then, separating the non-oligomerizable "inerts" intermediate the reactors, results in several important advantages of our combination MOG+MODL process. First, we can use a relatively low cost, low pressure MOG fluid bed reactor, operating preferably below 2170 kPa (300 psig). Second, essentially no $C_{10}^+$ components are fed to the secondary reactor. Third, the MOG reactor may be operated to maximize conversion so as to minimize the amount of $C_4^-$ olefins leaving the MOG reactor.

Unlike a fixed bed, the fluid-bed MOG reactor is relatively insensitive to temporary poisons such as nitrogen-containing compounds, and produces a relatively constant product distribution which is desirable for the operation of the secondary reactor. Operation of the MOG primary reactor is combined with a secondary reactor which, in the best mode, is a low cost high pressure MODL reactor operating in the liquid phase, the super-dense phase, or the gas phase, with a relatively easily oligomerized (particularly, dimerized and trimerized) $C_5^+$ feedstream. Close temperature control is afforded by operation of the fluid-bed in the turbulent regime (referred to as a "turbulent bed") allowing the most economical "make" of gasoline for feed to the MODL reactor, and distillate which bypasses the MODL reactor. In the fluid bed MOG reactor, an essentially uniform conversion temperature may be maintained (often with closer than ±5° C. tolerance) to ensure that the low activity of the catalyst is maintained in the desired range without depositing an undue amount of coke, and without significantly changing the gasoline product composition. Except for a small zone adjacent the bottom gas inlet, the midpoint measurement of conditions in the bed is representative of the entire bed, due to the thorough mixing achieved.

Moreover, in turbulent beds, fluidization is better at a higher fluidizing gas velocity, and with a higher level of the finer sizes of catalyst (see R. M. Braca and A. A. Fried, in *Fluidization*, D. F. Othmer, Ed. (Reinhold, New York, 1956), pp. 117–138; W. W. Kraft, W. Ulrich, W. O'Connor, ibid., pp. 184–211). This requires a significant amount of fines, from about 10 to 25% by weight (% by wt) having a particle size less than 32 microns. Since it is difficult to control the distribution and activity of catalyst fines it would seem at cross-purposes deliberately to require operation with a predetermined weight fraction of fines.

In the preferred embodiment, a $C_3$–$C_4$ olefin-rich light gas stream having a $C_3$–$C_4$ olefin content of at least 10% by wt, along with some higher olefins, ethylene (preferably less than 30% by wt), less than 50% by wt of $C_4^-$ alkanes, and up to 20% by wt hydrogen, is upgraded to gasoline with better than 85% per pass conversion of the olefins in a primary MOG reactor by catalytic conversion in a dense phase turbulent fluidized bed of solid acid ZSM-5 type of relatively low activity zeolite catalyst operating at a pressure below 1480 kPa (200 psig) in the absence of added hydrogen. The MOG effluent is partially condensed, and debutanized. In the distillate mode, substantially no $C_{10}^+$ components are fed to the MODL reactor. Irrespective of which embodiment of the distillate mode is used, more distillate than gasoline is produced in the MOD reactor with recycle of incompletely oligomerized streams, and often without recycle. In the lubes mode, gasoline is efficiently oligomerized in the MOL reactor to produce an MOL net product containing at least 15% by wt lubes in a single pass.

In the most preferred embodiment, the MODL reactor is a single stage fixed bed reactor, but may also be a fluid-bed, either of which preferably operates with a relatively higher activity catalyst than that used in the MOG reactor. For a fluid bed MODL reactor average equilibrated alpha is preferably <10; for a fixed bed MODL, fresh catalyst alpha is >60, and the average alpha preferably less than 40, as measured by a procedure analogous to that taught in U.S. Pat. Nos. 3,827,968 and 3,960,978 to Givens et al. In the fixed bed MODL reactor, the reactants are preferably in the liquid phase. The fluid-bed MODL reaction occurs outside the envelope of the phase diagram. Thus, the reactor may operate in the gaseous phase, or the super-dense phase.

Operation in the super-dense phase is at near-critical or super-critical temperature and pressure conditions; or, at subcritical pressure (below $P_{cr}$) and a temperature high enough to ensure that no liquid is present.

By "near-critical" conditions we refer to a pressure $P_{max}$, and a temperature $T_{max}$, the pressure and temperature respectively, at, or above which no liquid may be present. By "super-critical" conditions we refer to conditions above $P_{cr}$, $T_{cr}$ for the product, and outside the "envelope" of the phase diagram, as more fully described in our copending U.S. patent application Ser. No. 184,465 (Owen & Harandi) filed Apr. 20, 1988, the disclosure of which is incorporated by reference thereto as if fully set forth herein.

The particular operational mode of MODL reactor chosen, whether fixed bed or fluid-bed, and whether in the distillate or lubes mode, depends upon the economics of operation for a particular feedstock available in the refinery, and other considerations which pertain to operation of fixed beds rather than a fluid bed. The particular operating conditions chosen for a specific mode depend upon what particular boiling range of distillate is desired, and what minor amount of $C_5^+$ gasoline range hydrocarbons in the distillate is acceptable. Where essentially no gasoline is desired, the gasoline fraction separated from the overhead from the G/D splitter is partially recycled to the MOD reactor to boost distillate yield. In our aforesaid copending '926 patent application, the deethanizer produces a $C_3^+$ bottoms fraction which is flowed to the MOD reactor, and the distillate produced is separated in a G/D splitter placed after the MOD reactor. The result is that the MOD reactor operates at higher pressure because of the presence of the $C_3$ and $C_4$ paraffins, and, the feedstream to the reactor is not essentially distillate-free.

Operation of the Fluid-Bed MOG Reactor

In our combination of a single zone fluid-bed MOG reactor and a fixed bed MOGDL reactor, it is unexpectedly economical to operate the MOG reactor with a ZSM-5 type catalyst with a particle size in the range from about 20-100 microns, having a low average alpha in the range from about 1 to 20, relatively low WHSV in the range from about 0.1 to 5 $hr^{-1}$, a superficial velocity of about 0.1 m/sec to about 1 m/sec (0.3-3 ft/sec), a pressure below about 2170 kPa (300 psig), preferably in the range from about 1140 kPa (150 psig) to about 1480 kPa (200 psig), and a temperature below 400° C. (750° F.), preferably about 342° C. (650° F.), which is maintained with a feed inlet temperature in the range from 93°-150° C. (200°-300° F.) to convert at least 70% of the olefins, and preferably more than 80%, to highly olefinic $C_5^+$ components, mainly in the $C_6$-$C_{13}$ range, at a weight ratio of $C_5:C_5^= < 0.2$ and preferably less than 0.05. Particularly with respect to operating the MOG reactor to produce distillate, process conditions for the MOG are chosen to produce as high a $C_{10}^+$ content as is consistent with economical operation; and, when our process is to produce lubes, process conditions for the MOG reactor are chosen to yield as high an olefinic $C_5^+$ content as will favor maximum conversion to lubes.

Operation under the foregoing process conditions with the ZSM-type catalyst provides a controllable reaction severity index (R.I.) most preferably in the range from about 0.02 to 0.06. The R.I. is simply the ratio of alkane:alkene in the product, and is expressed herein as the ratio of $C_5:C_5^=$ in the effluent. It may also be expressed as the ratio of propane:propene, as for example in U.S. Pat. No. 4,547,616 to Avidan et al. Because we have defined R.I. with respect to pentane:pentene, we identify the ratio as "$(R.I.)_5$" and have so labelled it in FIG. 1 which illustrates the unique relationship of "$(R.I.)_5$" as a function of propene conversion in our MOG fluid bed. It is evident that at a propene conversion in the range from about 55% to 70%, the R.I. is about 0.04, and it is preferred to operate the MOG fluid bed with a R.I. in the range from about 0.05:1 to about 0.1:1.

The fluid-bed density in the MOG reactor which preferably operates to maximize the yield of gasoline range olefins under the foregoing conditions, is in the range exceeding 300 kg/m³ (19 lb/ft³), up to about 800 kg/m³ (50 lb/ft³), the higher the pressure, the higher the density of the gaseous phase, and the lower the bed density. The preferred particle density is preferably in the range from about 1.2-2.5 g/cc. A typical dense turbulent fluid bed has a minimum fluidization velocity of 0.014 m/sec (0.047 ft/sec) and operates at a superficial velocity in the range from about 0.2-0.61 m/sec (0.6-2 ft/sec). Operation with zeolite beta tends to maximize production of $C_{10}^+$ compounds.

Operation of the High Temperature Separator(s) (HTS)

The heat duty of the condenser for the MOG effluent is determined by the desired temperature of operation of this knock-out drum, which temperature in turn depends upon the bubble point of the liquid phase having the desired composition at the pressure at which it is to be separated.

In the first of the two modes of operation for producing distillate, a HTS, into which partially condensed MOD reactor effluent flows, separates recyclable components in the gaseous phase (in the HTS) to the MOG reactor; the liquid phase, of course, contains the distillate product. In lieu of this HTS, a second fractionator (for example, a second debutanizer) may be used if a more deliberate ('finer') separation of the components of the MOD effluent is justified by its (the second fractionator's) higher operating costs.

When operation is in the second distillate mode, the MOG effluent is preferably cooled to a temperature in the range from about 149° C. (300° F.) to about 260° C. (500° F.) so that the "wild" $C_{10}^+$ liquid stream (so termed because its composition varies wildly) includes not only a substantial amount of $C_5$-$C_9$ components, but also essentially all the $C_{10}^+$ distillate made in the MOG reactor.

Operation of the Debutanizer

The effluent from the MOG reactor is debutanized to remove inerts and $C_4^-$ hydrocarbons in a separation zone, preferably a conventional fractionator. The debutanizer operates at as low a pressure as practical to make an efficient separation of $C_4^-$ using ambient air, or, cooling tower water in the debutanizer's overhead condenser. In the distillate mode the operating pressure of the debutanizer is preferably in the range from about 790 kPa-1480 kPa (100-200 psig), and the temperature profile in the range from about 100° C.-250° C. (212°-482° F.) the latter being set by the operating pressure. The $C_4^-$ components are taken overhead, and, in the first distillate mode, the bottoms are pumped to raise the pressure to the requisite high pressure necessary to introduce the bottoms into the MODL reactor. Part of the $C_4^-$ overhead, or an intermediate draw-off from the debutanizer, may be recycled to the MOG reactor, the remaining overhead being flowed to a LPG plant. The debutanizer bottoms consists essentially of $C_5$-$C_9$ components, the precise composition of the bottoms depending upon the conditions at which the debutanizer is operated. In a particular mode of operation of the MOG reactor when conversion of $C_4^+$ olefins is relatively low (less than 85%), we may allow a major portion of the $C_4$ olefins along with n-butane and a minor portion of the isobutane to be sent to the bottom of the debutanizer to maximize overall process conversion.

In the second distillate mode, the gaseous phase from the HTS into which MOG effluent is flowed, is partially condensed and flowed to the debutanizer, the operating conditions of which will likely be different from those used if it is operated in the first distillate mode, because the flow of $C_{10}^+$ components to the debutanizer has been depleted by the HTS.

Operation of the Gasoline/Distillate (G/D) Splitter

The G/D splitter separates gasoline range hydrocarbons from distillate product in each of the two distillate modes of operation. In each case it separates gasoline range components (taken overhead) from distillate (bottoms). In the first distillate mode the G/D splitter is upstream of the MOD reactor; in the second, it is downstream. The overhead may be recycled to the MOG reactor, as is preferable in the first distillate mode; or, as is preferable in the second distillate mode, a portion of the overhead may be recycled to the MOG reactor, a portion may be recycled to the MOD reactor, and/or a portion ma be stabilized and blended into the gasoline pool.

The G/D splitter operates at about atmospheric pressure, the temperature profile in the G/D splitter being set by its operating pressure, the desired sepcifications of distillate to be recovered, and the amount of gasoline range hydrocarbons to be recycled to the MOG reactor.

Operation of the Fixed Bed MOD Reactor (distillate mode)

The lower gasoline range components are most preferably converted to $C_{10}{}^+$ distillate in a fixed bed MOD reactor. The higher the operating pressure, the higher the ratio of distillate to gasoline in the effluent. At the start of a cycle the temperature is most preferably about 205° C. (400° F.), and near the end of the cycle, about 288° C. (550° F.), based on the reactor inlet conditions. The operating pressure is preferably in the range from about 2857 kPa (450 psig) to about 5000 kPa (700 psig). The per pass conversion of the olefins is preferably such that the ratio of distillate to gasoline in the MOD effluent is >1 at a product selectivity of $C_{15}:C_{15}{}^=$ in the range from about 0.04 to about 0.2. The overall yield ("make") and/or quality of distillate may be maximized by recycling an insufficiently oligomerized portion of the effluent stream to the MOD reactor.

The MOD effluent is cooled, preferably by heat exchange in a feed/effluent exchanger. A distillate-rich stream from operation of either distillate mode of the process is flowed to the G/D splitter, and such undesired gasoline components as may be formed in the MOD reactor are taken from above the feed plate and recycled to the MOD reactor to maximize the production of distillate.

Operating conditions for the second (MOD) reactor are deliberately chosen to produce the maximum amount of $C_{10}{}^+$ distillate. Typically, the ratio of the product distillate to gasoline is 2:1, and may be as much as 10:1 in this process.

In the preferred embodiment, the MOD reactor is an oligomerization unit such as one disclosed in U.S. Pat. Nos. 4,456,779 and 4,497,968 (Owen et al), and 4,433,185 (Tabak), except that, in our invention, only a single operating MOD reaction vessel is required, though multiple reactors may be used if desired.

The MOD reactor, in the best mode for our present operation, is designed as a high-pressure fixed bed reactor. Typically, in carrying out the process in such a reactor, the $C_5{}^+$ stream is brought into contact with a medium pore zeolite catalyst having a silica to alumina ratio in the range from 12 to about 1000, more preferably from 30 to 70. Most preferred is a HZSM-5 catalyst having a constraint index in the range from 5–12, and an apparent alpha in the range from about 5 to about 100, the reactor operating with a WHSV in the range from about 0.1 to 5 $hr^{-1}$.

Our MOD reactor is most preferably operated at a pressure of about 3890 kPa (550 psig), an inlet temperature of about 204° C. (400° F.) and an outlet temperature of about 227° C. (440° F.), based on the start of cycle conditions. Despite such relatively low operating pressure and temperature conditions, operation in the best "distillate mode" produces more distillate than gasoline. The MOD reactor is oxidatively regenerated as described in the aforesaid patents, relevant portions of the disclosures of which are incorporated by reference thereto as if fully set forth herein.

To maintain the high per pass conversion and selectivity in the MOD fixed bed reactor, the catalyst is periodically regenerated in a conventional manner. While this is being done, the MOD reactor of course is taken off stream and replaced with one having freshly regenerated catalyst. Because of the high cost of a MOD reactor, only one may be used. In this case, the MOG reactor is operated to produce a higher octane gasoline, that is, at the upper limit of its operating temperature.

Operation of the Fixed Bed MOL Reactor (lubes mode)

A fixed bed MOL reactor is most preferably used to convert the $C_5{}^+$ bottoms from the debutanizer to lubes. The MOL fixed bed reactor oligomerizes a substantially $C_5{}^+$ (mainly $C_5$–$C_9$) stream, essentially free of $C_4{}^-$ and inert components, to lubes. The higher the operating pressure, the lower is the severity required to produce heavier lubes, most preferably beginning at about 5600 kPa (800 psig) and about 204° C. (400° F.), up to about 10450 kPa (1500 psig) and 288° C. (550° F.) The effluent from the MOL reactor is condensed and flowed to the D/L splitter in which the bottoms provides the desired lubes product. The overall "make" of lubes may be optimized by recycling an insufficiently oligomerized portion of the reactor effluent stream, taken as overhead and/or a side draw from the D/L splitter, to the MOL reactor.

Operation of the Distillate/Lubes (D/L) Splitter

The D/L splitter separates lighter than lubes (distillate and gasoline range hydrocarbons) which are taken overhead, from product lubes. A portion of the lighter components in the overhead may be recycled to the MOG reactor, and/or a portion may be recycled to the MOL reactor, depending upon the economics of operation.

The D/L splitter, most preferably operates under vacuum and stripping steam is used to remove light components from the lube product; the temperature profile in the D/L splitter is set by the pressure drop through it, the desired sepcifications of distillate to be recovered, and the amount of recycle to the MOG and MOL reactors.

Operation in the Distillate Mode of a Fluid-Bed MOD Reactor

In an alternative embodiment, the MOD reactor chosen may be a fluid bed particularly adapted for the production of distillate, operated in the vapor phase outside the phase envelope, or under super-dense conditions at or above $P_{max}$ and $T_{max}$, under which conditions it is critical that there be no liquid phase present, as more fully described in the aforesaid Ser. No. 184,465. It is essential that the MOD fluid-bed reactor be operated under conditions such that no liquid is present. Operation may be at subcritical pressure but at a temperature outside the phase envelope, under conditions which may not be super-dense. Alternatively, and more preferably, operation may be in the super-dense phase which requires that the pressure and temperature be maintained outside a critical region (critical P & T region) in the phase diagrams of either the feed, the product, or any intermediate.

This critical P & T region is defined by an arc circumscribed around the critical point, between the vertical through the critical point, and, the dew point curve of the phase diagram, the arc having a radius corresponding to about 344.5 kPa (50 psia). The fluid bed MOD operates outside a tightly circumscribed critical P & T region which region lies near, or above the apex of a phase diagram defining the critical point ($P_{cr}$, $T_{cr}$) of the mixture of hydrocarbons in the reactor. The operating P and T conditions of the MOD reactor may be supercritical (that is, both are above $P_{cr}$, $T_{cr}$ of the mixture); or, only one or the other may be below $P_{cr}$, $T_{cr}$; or, both may be below $P_{cr}$, $T_{cr}$; provided they are not in the critical P & T region. Operation at precisely $P_{cr}$, $T_{cr}$ conditions, or too close to them (within the critical P & T region), involves too high a risk of disturbance of desirable operation and formation of a liquid phase, and is therefore avoided.

The fluid-bed density in the MOD reactor operating to maximize the yield of distillate is in the range exceeding 500 kg/m$^3$ (31.1 lb/ft$^3$), up to about 1000 kg/m$^3$ (62.33 lb/ft$^3$). The preferred particle density is preferably in the range from about 1.2–2.5 g/cc. A typical super-dense fluid bed operates at a superficial velocity in the range from about 0.03–0.45 m/sec (0.1–1.5 ft/sec).

Since the MOD reactor is operated as a fluid bed in the turbulent regime, the content of catalyst fines is maintained in the range from about 5% to about 20% by wt, based on the weight of the catalyst in the MOD bed, the fines having a particle size less than 32 microns. Preferred operation of the fluid bed MOD reactor excludes a region circumscribed by about a 50 psia differential from $P_{cr}$, $T_{cr}$ of the hydrocarbon mixture in the bed, and bounded by the portion of the bubble-point-/dew-point curve downwardly inclined from said point. Under such high pressure conditions, the reaction is prejudiced in favor of oligomerization with a minimum of cracking of heavy $C_{10}^+$, so that particular ranges of temperatures are found most desirable for a "make" in the desired distillate range. The precise optimum combination of pressure and temperatures, along with WHSV, for a particular catalyst and feed, is best arrived at with such trial and error as one skilled in the art is enured to.

In a fluid-bed MOD reactor, the entire bed is in a fluid phase in which the solid acts both as catalyst and heat transfer sink. In this process, we regard the super-dense phase as being neither gas nor liquid, but for convenience and familiarity, we treat the oligomerization reaction as being a gas/gas reaction.

Operation in the Lubes Mode of a Fluid Bed MOL reactor

In an alternative embodiment, the MOL reactor chosen is a fluid bed operated in the super-dense phase, in a manner analogous to that described hereinabove for the fluid bed MOD reactor, except that the pressures will be higher than those used in the MOD fluid bed. The ranges for the MOL reactor are set forth hereinbefore.

In the preferred mode, both oligomerization reactors operate at low WHSV. The bed of catalyst, whether fixed or fluid, consists essentially of a finely divided medium pore zeolite metallosilicate catalyst having a constraint index in the range from 1 to 12, and a fresh catalyst activity (alpha) in the range from about 50 to 100. Additional details relating to the catalyst are set forth in the Owen et al '779 patent, the disclosure of which is incorporated by reference thereto as if fully set forth herein. The MOG reactor preferably operates at low severity and low activity (alpha) in the range from about 2 to about 20; and the MODL reactor preferably operates at even lower severity, but preferably higher alpha in the range from 5 to about 75; the MOG reactor operates in combination with a regenerator; if the MODL reactor is a fluid-bed, it too operates with a regenerator.

The improved operation of a conventional MOG reactor as the first stage of our novel process, comprises, (a) contacting light gas or light naphtha with a finely divided porous aluminosilicate catalyst having an average particle size in the range from about 20 microns to about 100 microns, a constraint index less than 12, preferably in the range from about 5 to about 12, and an operating alpha preferably in the range from about 2 to 15, said catalyst preferably maintained in a single zone turbulent regime MOG fluid-bed operating at a temperature in the range from about 260°–399° C. (500°–750° F.) and a pressure in the range from about 790–2860 kPa (100–400 psig) in the absence of added hydrogen, (b) flowing said light gas or naphtha through said MOG bed at a weight hourly space velocity (WHSV) in the range from about 0.1 to about 10 hr$^{-1}$, and preferably from 0.5 to 2 hr$^{-1}$, with a superficial vapor velocity in the range from about 0.1–1 m/sec (0.3 ft/sec–3 ft/sec), (c) maintaining a content of catalyst fines in the range from about 10% to about 20% by wt, based on the weight of the catalyst in the MOG bed, said fines having a particle size less than 32 microns, and, (d) converting at least 70% by wt of the olefins to produce a MOG effluent containing a major amount of $C_5^+$ (mainly $C_6$–$C_{13}$ hydrocarbons substantially free of aromatics and containing a major amount by weight of $C_5^+$ (pentanes, pentenes and heavier), and a minor amount of $C_4^-$ (butane, butenes and lighter), less than 1% of alkanes having been added to the alkane content of said feed due to conversion in the reactor, with pentane and pentene in a weight ratio up to about 0.2:1. The per pass selectivity is in the range from about 5 to 50%, and may be 80% or more, but typically is 20%.

Our preferred and unexpectedly beneficial process, namely combining the operation of a relatively high pressure fluid-bed MOG reactor upstream of a higher pressure MOD reactor, comprises, (a) operating the MOG reactor as described hereinabove, but at relatively low pressure in the range from about 1630 kPa (100 psig) to about 2170 kPa (300 psig), with a feed inlet temperature in the range from about 93° C. (200° F.) to about 150° C. (300° F.), and an outlet temperature in the range from about 288° C. (550° F.) to about 344° C. (650° F.), so as to produce a MOG effluent substantially free of aromatics and having a major proportion by weight of $C_5^+$ components, including at least 1 part by wt of $C_{10}^+$ components, and preferably 3 parts, for every 10 parts of $C_5-C_9$ components, (b) separating the $C_4^-$ components from the MOG effluent, (c) recovering product $C_{10}^+$ distillate components from the MOG effluent, and separating the $C_9^-$ components therefrom in a gas-phase/liquid-phase separation zone;

(d) contacting essentially only gasoline range $C_5-C_9$ components, substantially free of aromatics and $C_4^-$ components, with a finely divided porous aluminosilicate catalyst having a constraint index less than about 12, and an average operating alpha in the range from about 5 to about 20, in a fixed bed MODL reactor maintained at a temperature and under sufficient pressure to produce more $C_{10}^+$ components than gasoline, irrespective of the phase, whether liquid, gas, or gas/liquid, in which reaction occurs; and, optionally, in a super-dense MODL fluid-bed reactor operating in a single zone turbulent regime at or above $P_{max}$ and $T_{max}$ at which no liquid may be present, said MODL reactor operating in the absence of added hydrogen to counteract poisoning of the catalyst, at a WHSV in the range from about 0.1 to about 10 $hr^{-1}$, and preferably from 0.1 to 5 $hr^{-1}$, with a superficial space velocity in the range from 0.1 to 1 m/sec (0.3-3 ft/sec), and, (e) recovering a distillate or lubes stream from the MODL effluent leaving said MODL reactor, in which MODL effluent there is more $C_{10}^+$ product than gasoline.

Figure 2:
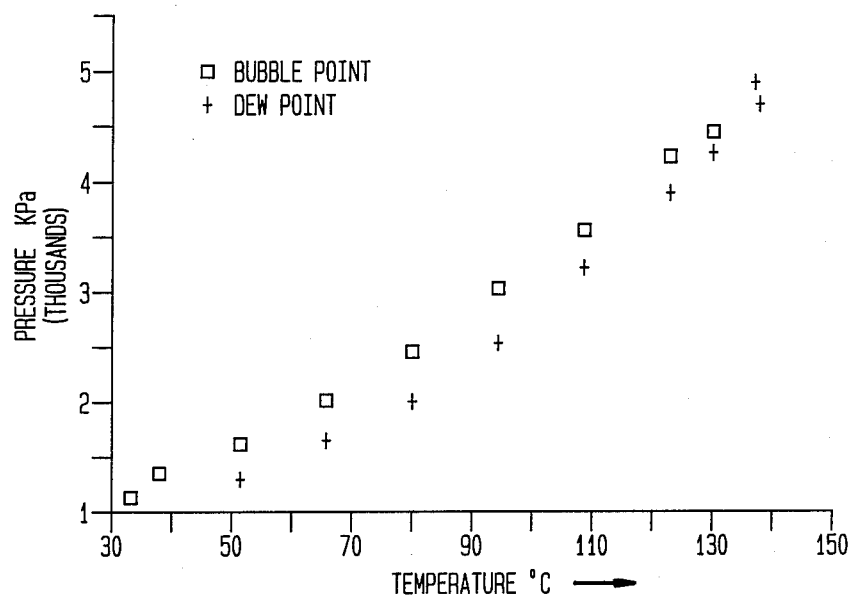
FIG. 2 is a phase diagram showing a plot of dewpoint and bubble-point curves for a typical light gas feedstock to be upgraded.

Referring now to FIG. 2 there is shown a plot of dew-point and bubble point curves for a light gas feed (as a phase diagram) at temperatures from about 37.8° C. (100° F.) and about 689 kPa (100 psia), to the critical point, about 132° C. (270° F.) and 4272 kPa (620 psia), the light gas having the following composition:

| | |
|---|---|
| $C_3=$ | 25.5% by wt. |
| $C_3$ | 7.6% |
| $C_4=$ | 43.7% |
| $C_4$ | 23.2% |

It is evident from the phase diagram for the feed, that above about 965 kPa (140 psia) there is less than about 23° C. (50° F.) separating the gas and liquid phases. The difference in temperature becomes progressively smaller as the pressure increases, becoming zero at the critical point.

The overhead from the debutanizer for a typical debutanized MOG effluent, is identified by the hydrocarbon components (in the overhead) listed herebelow:

| | |
|---|---|
| $C_2=$ | 0.2 % by wt. |
| $C_3=$ | 10.0 |
| $C_3$ | 8.2 |
| $C_4=$ | 31.5 |
| $C_4$ | 41.5 |
| $C_5^+$ | 8.0 |

The bottoms from a debutanizer for a typical debutanized MOG effluent is identified by the hydrocarbon components (in the bottoms) listed herebelow:

| | |
|---|---|
| $C_4^-$ | <10% by wt. |
| $C_5-C_9$ | remainder |
| $C_{10}^+$ | >20 |

Figure 3:
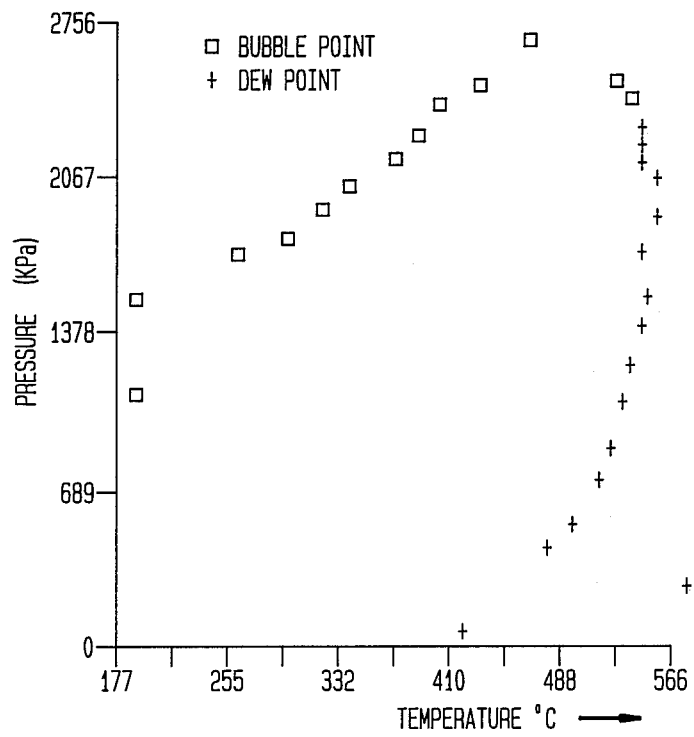
FIG. 3 is a phase diagram showing a plot of dewpoint and bubble-point curves for a desirable distillate produced in the MOD reactor from a desirable gasoline produced in the MOG reactor.

Referring now to FIG. 3 there is shown a plot of dew-point and bubble point curves in a phase diagram for a typical distillate produced from a debutanized MOG effluent. The phase diagram is for a range of temperatures from about 177° C. (350° F.) to the critical point, which is at about 500° C. (932° F.) and 2756 kPa (400 psia). It will be recognized that the precise composition of the distillate produced will depend upon the feed and the conditions of operation of the MOG and MOD reactors. Also, since lower paraffins are unconverted, it is desirable to keep their concentration in the feed to the MOG reactor as low as practical. A typical MOD product has the following composition:

| | |
|---|---|
| $C_4^-$ | <10.% by wt. |
| $C_5-C_9$ | remainder |
| $C_{10}^+$ | >50. |

It is evident from the phase diagram (FIG. 3) for the MOD product, that the phase envelope has expanded relative to that for the MOD feed (FIG. 2), and shifted towards higher temperatures. There is a much wider spread of temperature between the dew-point and bubblepoint curves at any given pressure except within about 344 kPa (50 psia) from $P_{cr}$. The difference in temperature becomes progressively smaller as the pressure increases, becoming zero at the critical point. The dew-point curve for the distillate is more vertiginous than that for the feed, actually showing a convex bulge.

In the fixed bed MODL reactor it is evident that the preferred liquid phase operation can be maintained at relatively low pressure and temperature, but the higher the pressure the better as lower temperatures are favored.

In the fluid bed MODL reactor, it is essential that the reactants be present in the super-dense phase without the formation of liquid, and it is critical that the dew-point curve never be traversed. In other words, P & T conditions for operation of the fluid bed MODL process must ensure that no liquid will be formed, whether from the feed, the product, or the intermediates formed during the reaction. Such conditions obtain at near-critical or super-critical conditions.

With the particular feed characterized by the phase diagram given in FIG. 2, the MOG reactor is operated in the gasoline mode to produce a $C_5^+$ gasoline range MOG effluent containing from 20%-35% by wt $C_4^-$, and preferably 3 or more parts distillate for 10 parts by wt of gasoline mde in the MOG reactor.

In the fixed-bed MODL reactor, the higher ratios of distillate:gasoline are produced at pressures above about 2756 kPa (400 psia), that is, super-critical pressure, and an outlet temperature below about 427° C. (800° F.), that is, sub-critical temperature. Most preferred operation of the fixed bed MODL reactor is in the liquid phase at a temperature below about 371° C. (700° F.). Typical operating conditions for the fixed bed reactor to produce a desirable distillate product is as follows:

| | |
|---|---|
| Temperature (inlet) | 204.4° C. (400° F.) at start of cycle (SOC) |
| Temperature (outlet) | 315.6° C. (600° F.) at end of cycle (EOC) |
| WHSV | 0.3 $hr^{-1}$ |

| | |
|---|---|
| Pressure (inlet) | 450+ kPa (985+ psia) |

There is no hydrogen added to the feed to the MODL reactor. It will be understood that the inlet temperature is typically lower than the bed temperature because the reaction exotherm raises the temperature, and heat transfer to the cooling coils in the bed is controlled to maintain the desired bed temperature.

In the fluid-bed MODL reactor, debutanized MOG effluent is fed to the MODL reactor operating above $P_{max}$ and $T_{max}$ of the debutanizer bottoms. As will be seen by reference to FIG. 3, the more the lower portion of the bubble point curves inwards from the vertical, the lower the pressure at which one can operate a fluid bed. In other words, the MODL reactor can operate in the superdense phase at a relatively lower pressure than prior art distillate or lubes modes embodiments, if the conditions are outside the critical P & T region (defined hereinabove). In operation with a typical $C_5+$ feed, in the particular instance where FIG. 3 is for a operation in a heavy distillate mode, the preferred operating pressure is at least 3100 kPa (450 psig), and $T_{max}$ is about 566° C. (1050° F.), though the reactor may be operated at as low a pressure as 2857 kPa (400 psig).

It will be appreciated that, whether the substantially $C_{10}+$-free feed is contacted in the secondary reaction zone operating as a fixed bed, movng bed, or fluid bed reactor, process conditions for its operation will be determined by the product desired in the effluent. Where the desired product is mainly distillate, the per pass conversion to distillate is typically at least 50%, and able to produce more distillate than gasoline per pass. Where the desired product is not mainly distillate, the per pass conversion to distillate may be in the range from about 20% to 50%, or less.

In a fluid-bed MODL reactor, oligomerization is effected in a single zone, that is, a single fluid bed operating in the superdense phase because the heat duty of the reaction exotherm is transferred to the cold feed and/or cooling fluid flowing through coils in the reactor. The operating conditions for the fluid bed reactor to produce the foregoing product is as follows:

| | |
|---|---|
| Temperature (outlet) | 260° C. (500° F.) |
| WHSV | 0.3 hr |
| Pressure (inlet) | 3445 kPa (500 psia) |

As in the fixed bed reactor, there is no hydrogen added to the feed, but unlike the fixed bed reactor, there is no liquid recycle. Since operating conditions of the fluid bed are chosen so that no liquid is formed during the reaction, it is essential that not only the more expanded phase envelope (compared to the relatively narrow one for the debutanizer bottoms) for the product be considered, but also all phase envelopes for the hydrocarbon intermediates formed during the reaction. The phase envelope for the product is expanded and shifted towards higher temperatures, because the product contains many more heavier molecules made during the reaction, than those in the feed.

When the desired product selectivity is obtained at a temperature above that corresponding to the dewpoint curve of the product, and above at least 204° C. (400° F.), the optimum (low) pressure may be used to minimize equipment cost. If the desired selectivity cannot be obtained at $T_{max}$, or a temperature just above it, then the operating pressure may need to be raised substantially above $P_{max}$. The combination of operating process conditions chosen will depend upon the particular specifications of product desired.

The MOG and MODL reactors are operable with shape selective medium pore catalysts exemplified by ZSM-5, ZSM-11, ZSM-12, ZSM-23, ZSM-35, ZSM-38, ZSM-48, zeolite beta, and other similar materials. U.S. Pat. No. 3,702,886 describing and claiming ZSM-5; U.S. Reisssue Pat. No. Re. 29,948 describing and claiming a crystalline material with an X-ray diffraction pattern of ZSM-5; and, U.S. Pat. No. 4,061,724 describing a high silica ZSM-5 referred to as "silicalite' are each incorporated by reference thereto as if fully set forth herein. Similarly, the disclosures relating to ZSM-11, ZSM-12, ZSM-23, ZSM-35, ZSM-38, and ZSM-48 set forth in U.S. Pat. Nos. 3,709,979, 3,832,449, 4,076,842, 4,016,245, 4,046,859, and 4,375,573, respectively, are each incorporated by reference thereto as if fully set forth herein.

In general the aluminosilicate zeolites are most effectively employed in our reactors. However, zeolites in which some other framework element which is isoelectronic to aluminum and which is present in partial or total substitution of aluminum can be advantageous. Illustrative of elements which can be substituted for art or all of the framework aluminum are boron, gallium, titanium, and, in general, any trivalent metal which is heavier than aluminum. Specific examples of such catalysts include ZSM-5 and zeolite Beta containing boron, gallium and/or titanium. In lieu of, or in addition to, being incorporated into the zeolite framework, these and other catalytically active elements can also be deposited upon the zeolite by any suitable procedure, e.g., by impregnation.

The aluminosilicates are preferred catalysts. These can be described as a three-dimensional framework of $SiO_4$ and $AlO_4$ tetrahedra in which the tetrahedra are cross-linked by the sharing of oxygen atoms whereby the ratio of total aluminum and silicon atoms to oxygen atoms is 1:2. In their hydrated form, the aluminosilicates may be represented by the formula:

$$M_{2/n}O:Al_2O_3:wSiO_2:YH_2O$$

wherein M represents at least one cation which balances the electrovalence of the tetrahedra, n represents the valence of the cation, w the moles of $SiO_2O$ and Y the moles of $H_2$. The cations can be any or more of a number of metal ions, depending upon whether the aluminosilicate is synthesized or occurs naturally. Typical cations include sodium, lithium, potassium, silver, magnesium, calcium, zinc, barium, iron, nickel, cobalt and manganese. Although the proportions of inorganic oxides in the silicates and their spatial arrangements may vary affecting distinct properties in the aluminosilicate, the main characteristic of these materials is their ability to undergo dehydration without substantially affecting the $SiO_4$ and $AlO_4$ framework.

Aluminosilicates falling within the above formula are well known and, as noted, include synthesized aluminosilicates, natural aluminosilicates, and certain caustic treated clays. Among the aluminosilicates are included zeolites, Y, L, S, X, levynite, erionite, faujasite, analcite, paulingite, noselite, phillipsite, datolite, gmelinite, leucite, scapolite, mordenite as well as certain caustic treated clays such as montmorillonite and kaolin families. The preferred aluminosilicates are those having pore diameters of greater than about 6 Å (Angstroms).

Aluminosilicates may be treated with a fluid medium or media in a known manner to include a wide variety of aluminosilicates both natural and synthetic which have a crystalline, or, combination of crystalline and amorphous structure. These "promoters" may be provided in the catalyst by impregnation or ion exchange.

Though the process of the invention is operable with any of the aluminosilicates the preferred catalyst is a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. These medium pore zeolites are favored for acid catalysis; however, the advantages of ZSM-5 type structures may be utilized by employing highly siliceous materials or crystalline metallosilicate having one or more tetrahedral species having varying degrees of acidity. The ZSM-5 crystalline structure is readily recognized by its X-ray diffraction pattern, which is described in U.S. Pat. No. 3,702,866 (Argauer, et al.), incorporated by reference herein.

The oligomerization catalysts preferred for use herein include the medium pore (i.e., about 5-7 Å) shape-selective crystalline aluminosilicate zeolites having a silica-to-alumina ratio of at least 12, a constraint index of about 1 to 12, preferred alpha during operation in the range from about 2 to about 15. In the MODL reactor the coked catalyst may have an apparent activity (alpha value) of about 2 to 25 under the process conditions to achieve the required selectivity and per pass conversion. Representative of the ZSM-5 type zeolites are ZSM-5, ZSM-11, ZSM-12, ZSM-22, ZSM-23, ZSM-35 and ZSM-38. Details about ZSM-5 are disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245; 4,046,839; 4,414,423; 4,417,086; 4,517,396 and 4,542,251, the disclosures of which are incorporated by reference thereto as if fully set forth herein. A typical zeolite catalyst component having Bronsted acid sites may consist essentially of aluminosilicate ZSM-5 zeolite with 5 to 95 wt % silica and/or alumina binder.

These siliceous zeolites may be employed in their acid forms, ion exchanged, or impregnated with one or more suitable metals, such as Ga, Pd, Zn, Ni, Co and/or other metals of Periodic Groups III to VIII. The zeolite may include a hydrogenation-dehydrogenation component (sometimes referred to as a hydrogenation component) which is generally one or more metals of group IB, IIB, IIIB, VA, VIA or VIIIA of the Periodic Table (IUPAC), especially aromatization metals, such as Ga, Pd, etc. Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (e.g., ionic $Ni^{+2}$, and a shape-selective medium pore acidic oligomerization catalyst, such as ZSM-5 zeolite) which components may be present in admixture or combined in a unitary bifunctional solid particle. It is possible to utilize an ethene dimerization metal or oligomerization agent to effectively convert feedstock ethene in a continuous reaction zone.

Certain of the ZSM-5 type medium pore shape selective catalysts are sometimes known as pentasils. In addition to the preferred aluminosilicates, the borosilicate, ferrosilicate and "silicalite" materials may be employed. It is advantageous to employ a standard ZSM-5, suitably modified, having a silica:alumina molar ratio in the range from 12:1 to 100:1, a constraint index in the range from 5 to 12, and with the aforesaid alpha value to convert substantially all the olefins in the feedstock.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02-1 micron being preferred, and an apparent crystal density in the range from about 0.6 to 1.9 $gm/cm^3$. In order to obtain the desired particle size for fluidization in the turbulent regime, the zeolite catalyst crystals are bound with a suitable inorganic oxide, such as silica, alumina, etc. to provide a zeolite concentration of about 5 to 95 wt %. In the description of preferred embodiments a 25% HZSM-5 catalyst contained within a silica-alumina matrix and having a fresh alpha value of about 80 is employed unless otherwise stated.

It is advantageous to employ a particle size range consisting essentially of 1 to 200 microns. Average particle size is usually about 20 to 100 microns, preferably 50 to 100 microns. The optimum particle size distribution is obtained with a mixture of larger and smaller particles within the above-specified range, having from 5-20% by weight fines. Close control of distribution is maintained with the fines in the size range less than 32 microns.

The average particle density of the catalyst as used may be tailored for optimum fluid-bed operation by compositing it with a matrix component of appropriate density. Such matrix components which provide particles of progressively increasing overall packed density are silica, alumina, beryllia, magnesia, barium oxide, zirconia, and titania, yielding values of from about 2.2 $gm/cm^3$ for silica, up to about 5.9 $gm/cm^3$ for zirconia. In our MODL reactor, the overall packed density of medium pore zeolite particles so composited, including the matrix component, can advantageously vary from about 0.6 to about 4 $gm/cm^3$, more preferably from about 2 to about 3 $gm/cm^3$.

Several useful parameters contribute to fluidization in the turbulent regime in accordance with the process of the present invention. When employing a ZSM-5 type zeolite catalyst in fine powder form such a catalyst should comprise the zeolite suitably bound or impregnated on a suitable support with a solid density (weight of a representative individual particle divided by its apparent "outside" volume) in the range from 0.6-2 g/cc, preferably 0.9-1.6 g/cc. When these solid particles are placed in a fluidized bed where the superficial fluid velocity is 0.06-0.5 m/s, operation in the turbulent regime is obtained. Those skilled in the art will appreciate that at higher pressures in the range, a lower gas velocity may be employed to ensure operation in the turbulent fluidization regime.

Figure 4:
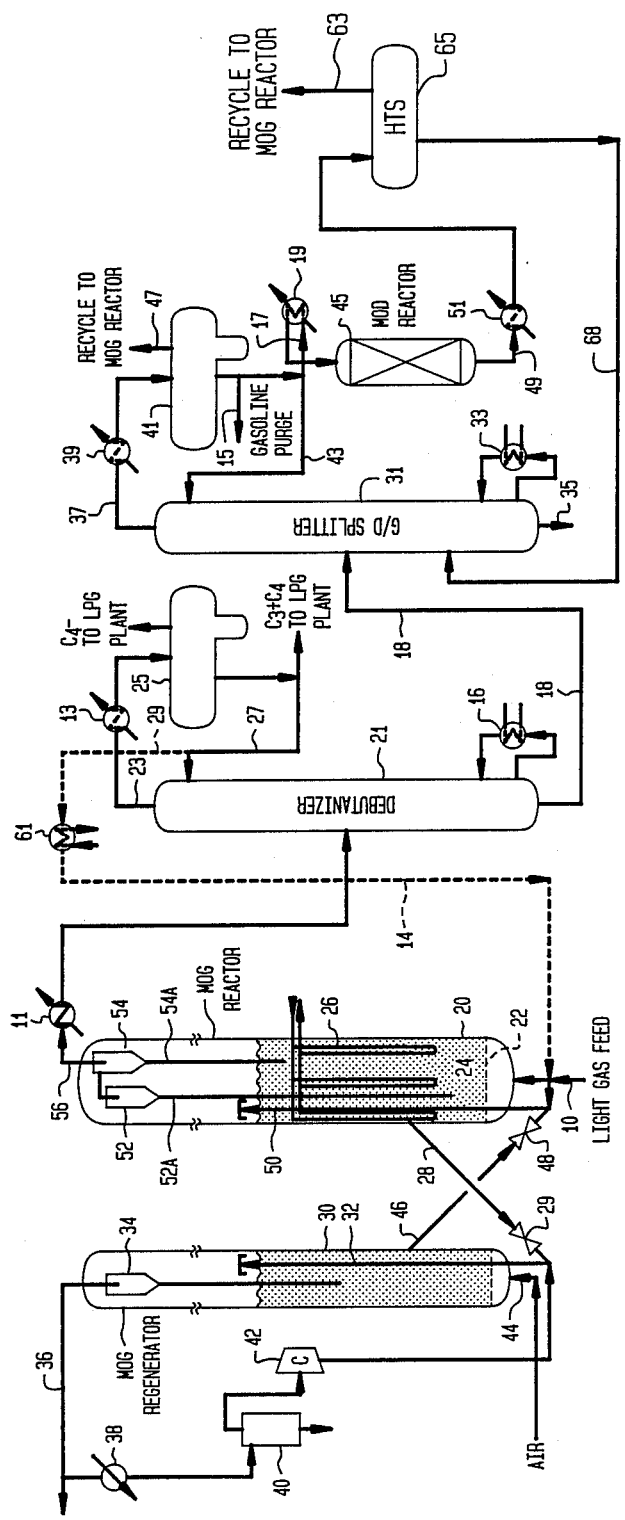
FIG. 4 is a flow diagram for the process in the first distillate mode, schematically illustrating the operational relationship of a MOG reactor, a condenser for the MOG effluent, a debutanizer, and a G/D splitter placed upstream of the MOD reactor. The fluid bed MOG reactor has associated with it a regenerator in which coked up catalyst is oxidatively regenerated and returned to the reactor, either periodically, or continuously.

Referring now to the first embodiment for operating in the distillate mode, illustrated in FIG. 4, a light-gas feed rich in $C_3-C_4$ olefins passes, through conduit 10, into MOG reaction vessel 20, with the main flow being directed through the bottom inlet for distribution through grid plate 22 into the fluidization zone 24 which is at 100-250 psig. The light-gas feed at an inlet temperature of about 200°-400° F. contacts the turbulent bed 24 of finely divided catalyst particles. MOG reactor 20 is provided with heat exchange tubes 26, which may be arranged as several separate heat exchange tube bundles so that temperature control can be separately exercised over different portions of the fluid catalyst bed. The bottoms of the tubes are spaced above feed distributor grid 22 sufficiently to be free of jet action by the charged feed through the small diameter holes in the grid. Alternatively, a substantial portion of the reaction heat can be removed by using cold feed. Baffles may be added to control radial and axial mixing. Although depicted without baffles, the vertical reaction zone can contain open end tubes above the grid for maintaining hydraulic constraints, as disclosed in U.S. Pat. No. 4,251,484 (Daviduk and Haddad) Heat released from the reaction may also be controlled by adjusting feed temperature in a known manner.

Catalyst outlet means 28 is provided for withdrawing catalyst from above bed 24 and passing the catalyst for regeneration in vessel 30 via control valve 29. The partially deactivated catalyst is preferably stripped with an inert gas (steam or nitrogen) in a stripper (not shown), and oxidatively regenerated by controlled contact with air or other regeneration gas at an elevated temperature in a fluidized regeneration zone to remove carbonaceous deposits and restore acid activity. The catalyst particles are entrained in a lift gas and transported via riser tube 32 to near the top of vessel 30. Air is distributed at the bottom of the bed to effect fluidization, with oxidation byproducts being carried out of the regeneration zone through cyclone separator 34, which returns any entrained solids to the bed. Flue gas is withdrawn via top conduit 36 for disposal; however, a portion of the flue gas may be recirculated via heat exchanger 38, separator 40, and compressor 42 for return to the vessel with fresh oxidation gas via line 44 and as lift gas for the catalyst in riser 32.

Regenerated catalyst is passed to the reaction vessel 20 through conduit 46 provided with flow control valve 48. The regenerated catalyst may be lifted to the catalyst bed with pressurized feed gas, through catalyst return riser conduit 50. Since the amount of regenerated catalyst passed to the reactor is relatively small, the temperature of the regenerated catalyst does not upset the temperature constraints of the reactor operations in significant amount. A series of sequentially connected cyclone separators 52, 54 are provided with diplegs 52A, 54A to return any entrained catalyst fines to the lower bed. These separators are positioned in an upper portion of the reactor vessel containing dispersed catalyst phase 24. Filters, such as sintered metal plate filters, can be used alone or in conjuction with cyclones.

Under optimized process conditions, the turbulent bed has a superficial vapor velocity of about 0.1 to about 0.4 (m/sec). At higher velocities, entrainment of fine particles may become excessive and beyond about 2 m/sec the entire bed may be transported out of the reaction zone.

A typical preferred dense turbulent bed has an operating density of about 550 to 1200 kg/m$^3$, measured at the bottom of the reaction zone, becoming slightly less dense toward the top of the reaction zone, due to pressure drop and particle size differentiation. Pressure differential between two vertically spaced points in the reactor volume may be measured to obtain the average bed density at such portion of the reaction zone.

By virtue of the turbulence experienced in the turbulent regime, gas-solid contact in the catalytic reactor is improved, typically providing 80% conversion or more of $C_3$-$C_4$ alkenes, enhanced selectivity, and temperature uniformity. One main advantage of this technique is the inherent control of bubble size and characteristic bubble lifetime. Bubbles of the gaseous reaction mixture are small, random and short-lived, thus resulting in such good contact between the gaseous reactants and the solid catalyst particles that typically, more than 95% of the butenes and about 99% of the propene is converted. The WHSV and uniform contact provides a close control of contact time between gas and solid phases, typically about 3 sec to 1 min.

The hot gaseous MOG effluent, comprising mainly $C_5^+$ olefins with some $C_2$-$C_4$ olefins, aromatics, paraffins and naphthenes, hydrogen and nitrogen, is separated from catalyst particles in the cyclone separating system 52, 54, and passes through line 56 to a condenser means 11 in which, preferably, a minor amount by wt of the $C_5$-$C_9$ intermediate hydrocarbons, and substantially all the $C_{10}^+$ is condensed and flowed to a first fractionator, the debutanizer 21. The debutanizer 21 is provided with an overhead condenser 13 and a reboiler 16, and the usual accessories (not shown). Bottoms from the debutanizer is a mainly $C_5^+$ stream 18, while the overhead is a $C_4^-$ stream which passes through line 23 into the overhead condenser 13 where it is condensed. The condensate flows into the reflux drum 25 from which a portion is refluxed through reflux line 27 to the top of the column 21, the remaining portion being flowed off-site to a LPG plant. Vapor leaves the reflux drum 25 through line 19 and is also flowed off-site to the LPG plant. If the yield of $C_5^+$ gasoline range debutanizer bottoms is to be maximized, a portion of the condensate 27 is preheated, preferably by heat exchange in an exchanger 61, and recycled through recycle line 14 (shown in phantom outline) to the MOG reactor.

The $C_5^+$ debutanizer bottoms is pumped through line 18 to the G/D splitter 31 equipped with reboiler 33. The withdrawn bottoms is $C_{10}^+$ distillate product which is flowed through line 35 to storage. The overhead from the G/D splitter leaves through line 37 and is condensed in condenser 39 into reflux drum 41 from which it is typically split into three portions. A first portion is refluxed, as reflux stream 43, to the G/D splitter. A second portion (feed for the MODL reactor) is pumped under sufficiently high pressure through a feed preheat line 17 into a MODL feed heat exchanger 19 to heat the feed, without vaporizing it, to the desired inlet temperature at which it is to be introduced into the MOD reactor 45 (illustrated as a single fixed bed). The MOD reactor is preferably operated so that at least 50%, and preferably 80% or more of the olefins in the feed is converted to $C_{10}^+$ components. The remaining third portion is a gasoline purge 15. Olefin-containing vapor from the drum 41 may be recycled through line 47 to the MOG reactor 20 to ensure that the net yield of distillate is higher than the yield of gasoline.

The effluent from the MOD reactor is flowed through line 49 and partially condensed in heat exchanger 51 before it is flowed into a HTS 65 where the $C_4^-$ olefins leaving the HTS as the gaseous phase in line 63, are recycled to the MOG reactor, or the MOG reactor effluent. The liquid phase from the HTS 65 consist essentially of $C_5^+$ hydrocarbons which are returned through line 68 to the G/D splitter.

The MOG reactor is designed as a pressure vessel required to contain a turbulent fluid-bed of catalyst desirably in the range from about 3–20 meters in height, preferably about 8 meters, and, operates at relatively low WHSV, preferably less than 10 hr$^{-1}$. Fine particles may be included in the bed, especially due to attrition, and the fines may be entrained in the product gas stream. A typical turbulent bed may have a catalyst carryover rate of about 1.5 times the reaction zone inventory per hour. If the fraction of fines becomes large, a portion of the carryover may be removed from the system and replaced by larger particles. It is desirable to have a fine particle separator such as a cyclone and/or filter means, disposed within or outside the reactor shell to recover catalyst carryover and return this fraction continuously to the bottom of the reaction zone for recirculation at a rate of about one catalyst inventory per hour. Optionally, fine particles carried from the reactor vessel entrained with effluent gas can be recovered by a sintered metal filter operating at the MG reactor conditions.

The operation of the turbulent MOG fluid bed in the dense phase produces a remarkably low coking rate, generally less than 0.05 wt % of the olefins in the feed, which low rate allows one to operate the bed without regeneration for a long period of time. In some instances periodic regeneration may be a preferred mode of operation. If not continuously regenerated, the coke content will gradually increase to about 15% by wt of the catalyst, at which point the run is desirably terminated.

When continuous regeneration is chosen, the regenerator will be operated at the highest pressure at which effective decoking can be quickly effected without exceeding a temperature deleterious to the activity of the regenerated catalyst. Typically, the regeneration pressure is in the same range as that for the reactor. Whether withdrawal of coked-up catalyst is periodic or continuous, the activity of the regenerated catalyst is maintained such that the weight ratio of $C_3$–$C_5$ alkanes:alkenes in the primary effluent is in the range from about 0.04:1 to about 0.2:1 under conditions of reaction severity to effect feedstock conversion.

The per pass conversion of lower olefins to $C_5^+$ hydrocarbons is preferably at least 70%, and typically better than 90%, with a selectivity of about 80%. Because $C_4^-$ hydrocarbons in the MOG effluent are undesirable, the highest practical per pass conversion which can be obtained is dictated by the economics of operating the MOG reactor at a pressure below 2070 kPa (300 psig). Typically, the ratio of $C_5^+$ to $C_4^-$ range hydrocarbons is held in the narrow range of from about 5:1 to about 10:1.

The feed to the MOG reactor will preferably be preheated by the internal coils 26 through which liquid feed is pumped under sufficient pressure to provide a gaseous feed to the respective beds, and at a temperature not much lower than about 20° C. from the desired operating temperature in each bed. The MOG regenerator will typically operate in the range from about 371° C.–510° C. (700° F.–950° F.), and the flue gas from the regeneration zone will be cooled to a sufficiently low temperature in the range from about 35° C.–50° C. (95° F.–122° F.), so that a portion of it may be compressed and recycled to the regeneration zone, and the remainder discharged.

Figure 5:
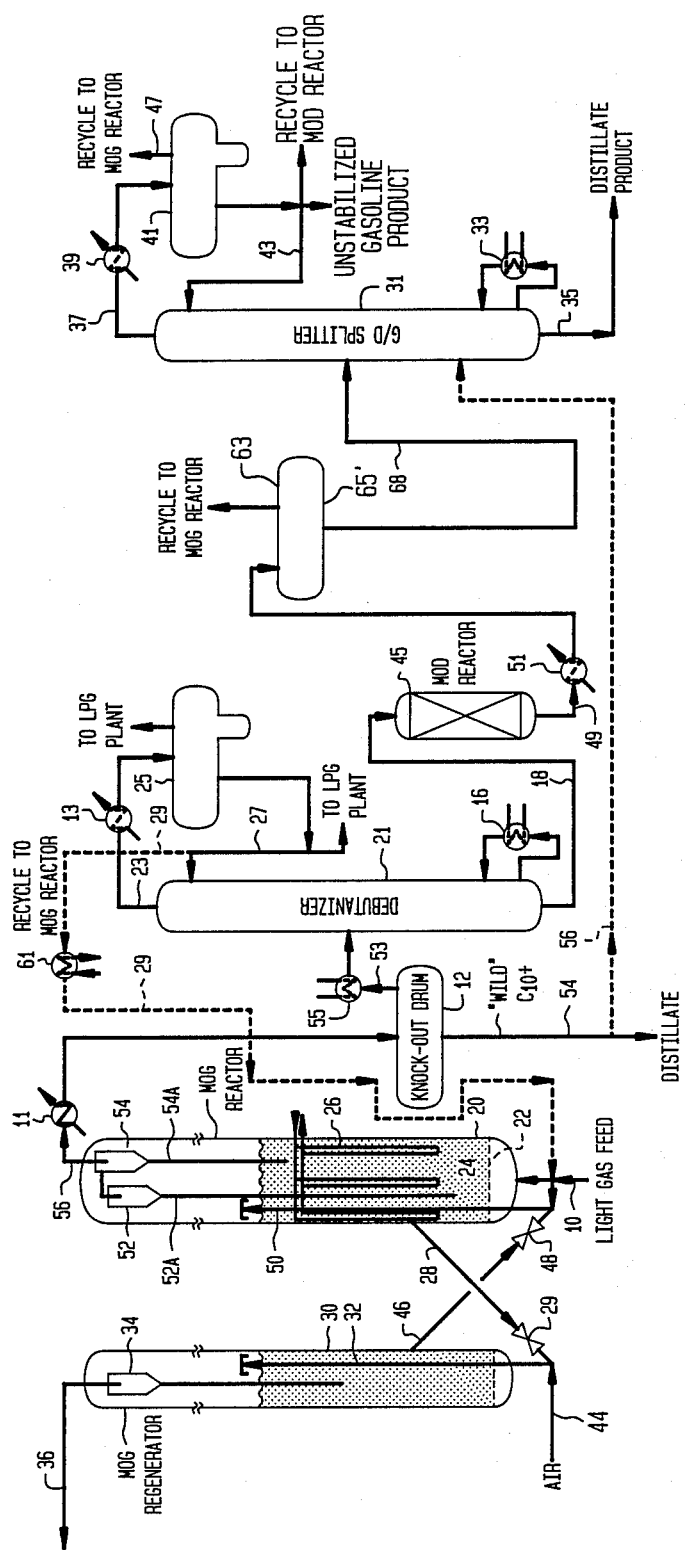
FIG. 5 is a flow diagram for an alternative embodiment of the process in the distillate mode, schematically illustrating the operational relationship of a MOG reactor, a partial condenser for the MOG effluent, a first HTS, such as a knock-out drum, a debutanizer, and a G/D splitter placed downstream of the MOD reactor. Effluent from the MOD reactor is separated in a second HTS or second debutanizer. As in the prior embodiment, the fluid bed MOG reactor has associated with it a regenerator.

Referring now to the second embodiment for operating in the distillate mode, illustrated in FIG. 5, the light-gas feed is oligomerized in the MOG reaction vessel 20, as in the first embodiment, and the effluent is partially condensed so that substantially all the $C_{10}^+$ hydrocarbons are condensed and flowed to a HTS 12 ("first" HTS) which is a vapor-liquid phase separation zone (knock out drum). In HTS 12, the liquid phase is separated from the vapor phase which is flowed through line 53 and preferably partially condensed in exchanger 55 before being flowed into the debutanizer 21. The separated liquid condensate is the "wild" $C_{10}^+$ cut 54 which contains a substantial amount of $C_5$–$C_9$ hydrocarbons, a portion or all of which may be flowed through line 56 to the lower section of the G/D splitter 31, the remaining portion being taken as relatively lower grade distillate product than that obtained as bottoms from the G/D splitter 31. Alternatively, the entire wild cut may be taken as a wild light distillate if none of the wild cut is flowed to the G/D splitter.

As in the first embodiment, a portion of catalyst from the MOG reaction vessel is either periodically or continuously removed for regeneration in regenerator 30. Because of the relatively small amount of catalyst to be regenerated, the low coke formation on the catalyst, and the relatively small amount of hydrocarbons left in the catalyst, the conditions under which the catalyst may be regenerated are such that air may be used to regenerate it without exceeding the explosive limits within the regenerator. Therefore no recycle of a portion of the flue gas from the regenerator is necessary, and this "air alone" mode of regeneration is preferred.

The bottoms from debutanizer 21, substantially free of $C_{10}^+$ components is flowed to the MOD reactor 45, operating as described hereinabove.

Effluent 49 from the MOD reactor 45 is partially condensed in exchanger 51 and flowed to a HTS 65' ("second" HTS) from which the gaseous phase is recycled to the MOG reactor or the debutanizer 21. The separated liquid phase from the HTS 65' is flowed to the G/D splitter 31' now located downstream of the MOD reactor, and the distillate product recovered as before. The conditions of temperature and pressure in the HTS drum 65' are selected so as to tailor the content of $C_{10}^+$ hydrocarbons (in the liquid phase) to be flowed to the G/D splitter, and also to flash as much of the $C_9^-$ components as might desirably be recycled to the MOG reactor or the debutanizer 21.

Instead of the HTS 65', an additional fractionator such as a (second) debutanizer (not shown) may be used to make a more precise separation than can be made in the second HTS.

As before, the bottoms from the G/D splitter is product distillate, but of closely controllable grade, and the overhead of the G/D splitter is a gasoline-containing stream which is at least partially condensed in exchanger 39 and flowed into drum 41. The vapor separating from the liquid in the drum 41 is recycled to the MOG reactor or debutanizer 21. A portion of the liquid is refluxed through line 43 to the G/D splitter and the remaining portion withdrawn as unstabilized gasoline product, and still another portion may be recycled to the MOD reactor to optimize conversions to distillate.

Figure 6:
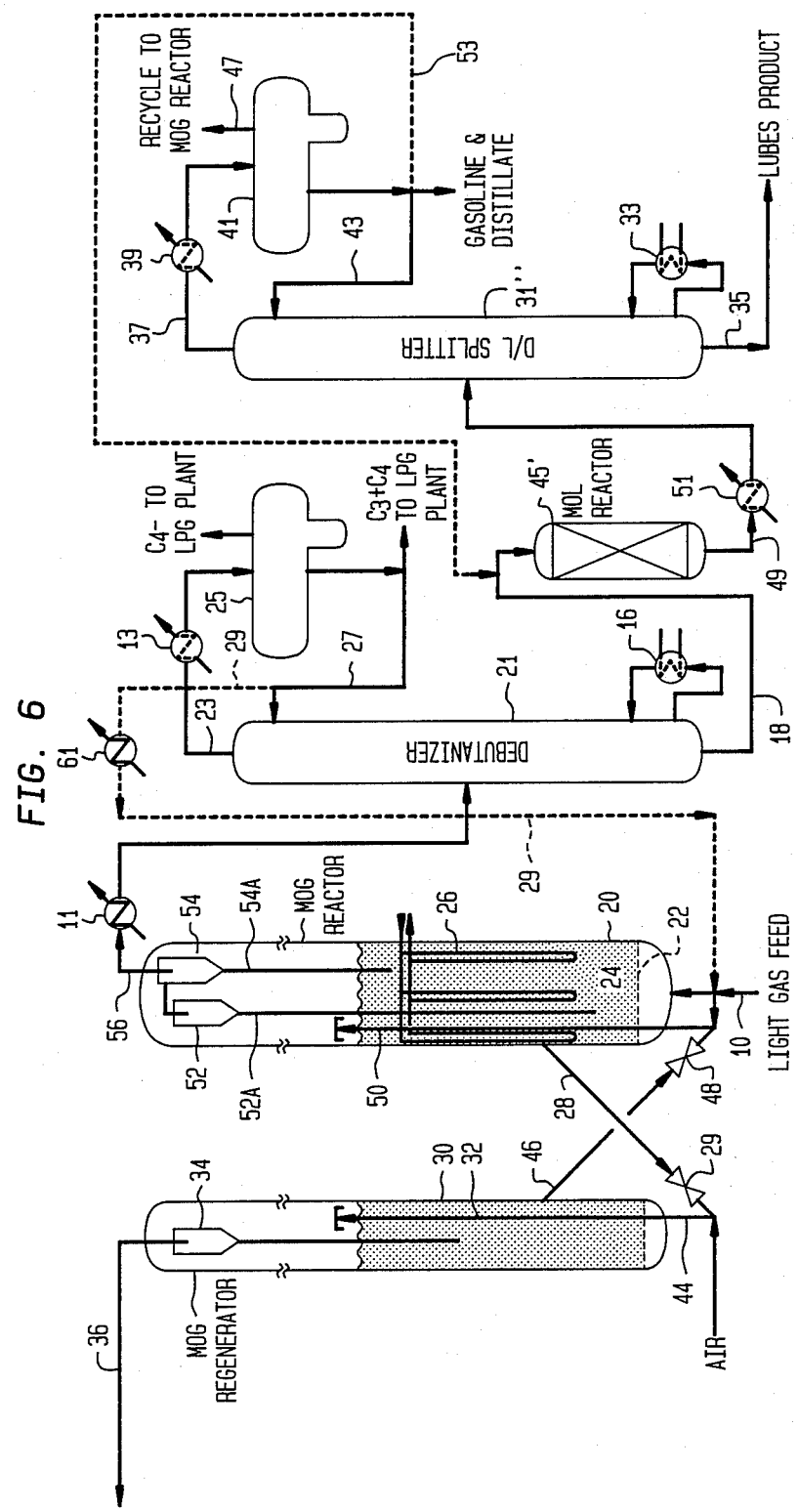
FIG. 6 is a flow diagram for the process in the lubes mode, schematically illustrating the operational relationship of a MOG reactor with associated regenerator, as before, a partial condenser for the MOG effluent, a debutanizer, and a D/L splitter placed downstream of the MOL reactor.

Referring now to FIG. 6 for operation in the lubes mode, there is schematically illustrated a process flowsheet for using a similar, if not the same, MOG reactor as used in the distllate mode, but with different processing of the effluent. Because conditions of operation of the similar equipment used will likely be different from those in FIGS. 4 and 5, such equipment is identified in the flowsheet by numerals corresponding to the numerals used to identify the corresponding equipment in the distillate mode. The MOL reactor and the D/L splitter however are identified by singly and doubly primed numerals, respectively to draw attention to the fact that the conditions of operation of the MOL reactor 45' and D/L splitter 31" are substantially different from those for the MOD reactor 45, and G/D splitters 31 and 31', respectively.

Referring further to FIG. 6, the primary effluent from the MOG reactor is cooled and flowed, through line 56, directly to debutanizer 21. As before the debutanizer is operated conventionally with provisions for at least partially condensing the overhead to a temperature in the range from about 38° C. (100° F.) to about 100° C. (212° F.), analogous to those described in FIG. 4, so that olefins in the liquid phase of the overhead drum 25 are mainly $C_3$ and $C_4$ which are pumped to the LPG plant. As before, a portion of the overhead may be recycled to the MOG reactor to maximize conversion to $C_5^+$ gasoline. The debutanizer bottoms consist essentially of $C_5^+$ components which include essentially all $C_5^+$ gasoline and $C_{10}^+$ distillate made in the MOG reactor. Liquid debutanized bottoms is optionally preheated and pumped with a high-pressure pump (not shown) to bring the bottoms to a predetermined pressure before it is flowed through line 18 to fixed bed MOL reactor 45'.

The per pass conversion in the MOL reactor is at least 55% of the olefins in the predominantly olefinic $C_5^+$ intermediate stream, and typically, the effluent from the MOL reactor 45' contains more $C_{10}^+$ than gasoline, formed in a single pass, with at least 80% conversion of olefins in the feed stream to 45'. The MOL effluent is flowed through line 49 to exchanger 51 where it is cooled to a preselected temperature before being introduced into D/L splitter 31". The D/L splitter 31" is provided with overhead condenser 39 and reboiler 33; or, in lieu of a reboiler, with stripping steam (not shown) to minimize degradation of the lubes. Bottoms from the D/L splitter is lubes product which is led through line 35 to storage.

Overhead taken from the D/L splitter is flowed through line 37, partially condensed in exchanger 39 and collected in reflux drum 41. Since the effluent from the MOL reactor typically contains a minor proportion by weight of $C_4^+$ olefins which leave as vapor from the reflux drum, the vapor is recycled through line 47 to the MOG reactor. A portion of the liquid condensate from the reflux drum is refluxed through line 43 to the top of the D/L splitter, the remaining being taken as mixed gasoline and distillate. If desired, a portion of the mixed gasoline and distillate may be recycled to the MOL reactor through line 53 (shown in phantom outline) to maximize the yield of lubes so that the net yield of lubes is higher than the gasoline yield; alternatively, the mixed gasoline and distillate may be flowed to a finishing fractionator (not shown) to provide a product distillate stream having desired more controlled specifications, with the option of recycling the gasoline separated.

It will be appreciated that the design, construction and operating conditions of a commercial oligomerization reaction vessel will be dictated by the economics of producing gasoline, distillate or lubes, as the case may be, and the optimum operating conditions will be dictated by the conversions sought. If it is desired to maximize conversion to distillate or lubes, appropriate streams containing oligomerizable components, are recycled.

COMPARATIVE EXAMPLE

Effluent from a MOG reactor operating as described hereinabove, is cooled and debutanized to provide a $C_5-C_9$ feedstream, substantially free of $C_4^-$ and $C_{10}^+$ components, to a secondary MOD fixed bed reactor operating with a H-ZSM-5 or zeolite beta catalyst having an average alpha of about 10-30, at an average pressure and temperature of 6785 kPa (970 psig) and 232° C. (450° F.), respectively, with a residence time of 0.35 hr. The composition of the effluent from the MOD reactor is set forth herebelow for a single pass, under the heading "Novel" process. The analysis of the MOD effluent is based on conversion of all the olefins (100%) in the MOG reactor. The feed $C_3-C_4$ hydrocarbon feed to the MOG reactor is characterized by the phase diagram in FIG. 2.

For comparison, assuming 100% conversion in the process of the '926 application, the entire essentially $C_2^+$ MOG effluent is sent to the MOD reactor. The liquid phase from the knock-out drum and the bottoms from the deethanizer are combined and fed to the MOD secondary reactor operating under the same process conditions as for the run described immediately hereinabove for the "Novel" process. The composition of the effluent from the MOD reactor is set forth herebelow for a single pass, under the heading "'926" process, and as before the basis is 100% conversion of olefins in the MOG reactor.

|  | Feed to MOD, wt % | | MOD effluent, wt % | |
| --- | --- | --- | --- | --- |
|  | '926 | Novel | '926 | Novel |
| $C_2=$ | 0.2 | | | |
| $C_3$ | 8.2 | | 0.1 | |
| $C_4=$ | | | 0.8 | 0.5 |
| $C_4$ | 24.0 | | | |
| C5-C10 | 64.2 | 94.8 | 58.9 | 40.6 |
| $C_{11}+$ | 3.6 | 5.2 | 40.2 | 58.9 |

As is evident, the single pass conversion with the novel process, without recycle of olefins to the MOG reactor, produces more distillate than gasoline. With recycle to the MOD reactor of the $C_5-C_9$ gasoline range hydrocarbons, to convert the unconverted olefins in the recycled stream, the conversion generally exceeds 70%.

An analogous operation of the process in the lubes mode produces unexpectedly higher per pass conversion of olefins to lubes in a MOL secondary reactor operating in the range taught hereinbefore.

Operation of the MOD reactor at or above $P_{max}$ and $T_{max}$

In this illustrative example, the process is carried out in a very high pressure reactor in which debutanized MOG effluent obtained as described in the comparative examples hereinabove is brought into contact with a medium pore H-ZSM-5 zeolite catalyst having a silica to alumina ratio of about 70. The H-ZSM-5 catalyst has a constraint index of about 10; and, an equilibrated alpha of about 10. The catalyst is maintained in a super-dense phase in a fluid-bed at supercritical conditions at a pressure of 6787 kPa (985 psia) and, with the inlet temperature of the feed being 254.4° C. (490° F.), the temperature of the bed is maintained at 315.5° C. (600° F.). The $C_5$–$C_9$ debutanized effluent, substantially free of $C_4^-$ and $C_{10}^+$ components, is flowed through the MOD reactor at a WHSV of 0.3 hr$^{-1}$. The results for a single pass, that is, without any recycle of $C_5$–$C_9$ gasoline range hydrocarbons, are analogous to those obtained with the fixed bed MOD reactor.

For comparison, the same debutanized feed is flowed through a series of fixed bed reactors operating at substantially the same inlet pressure of 985 psia, and at temperatures of 254.4° C., 248.9° C., and, 243.3° C., and a diluent rate (assumed inert) of 105,500 lb/hr, as taught in the prior art. The conversion per pass is much lower, as is the ratio of distillate to gasoline in the effluent from the third fixed bed.

Having thus provided both a general and a detailed discussion of the invention, it is to be understood that no undue restrictions are to be imposed by reason thereof except as provided by the following claims.

We claim:

1. In a catalytic process comprising multistage reaction zones for oligomerizing olefin-containing FCC gas, light gas having from 3 to 5 carbon atoms ($C_3$–$C_5$) or light naphtha ($C_5$–$C_7$) feedstock, into a $C_{10}^+$ aliphatic hydrocarbon product, including maintaining a primary reaction zone containing zeolite catalyst particles in a low severity reactor bed; passing said feedstock upwardly through said primary reaction zone in a single pass at sufficiently high pressure and temperature to provide reaction severity conditions sufficient to oligomerize lower alkenes to intermediate range olefins mainly in the $C_5$–$C_9$ range; withdrawing from said primary reaction zone a primary effluent containing olefins with a major amount by weight of $C_5^+$ olefinic hydrocarbons, and, a minor amount of $C_4^-$ olefinic hydrocarbons; and, further oligomerizing said $C_5^+$ hydrocarbons in a secondary reaction zone by contacting with a bed of medium pore shape selective acid oligomerization catalyst, further to upgrade them to said $C_{10}^+$ product; the improvement comprising,
   (a) separating $C_4^-$ substantially light gas components from said primary effluent so as to provide a predominantly olefinic $C_5^+$ intermediate stream substantially free of said $C_4^-$ components and comprising at least 1 part by weight of distillate per 10 parts of gasoline;
   (b) contacting said intermediate stream with said oligomerization catalyst in said secondary reaction zone under oligomerization conditions to produce a predominantly $C_{10}^+$ effluent, and,
   (c) recovering said $C_{10}^+$ aliphatic product.

2. The process of claim 1 wherein said primary reaction zone operates as a fluidized bed at moderate pressure below 2170 kPa (300 psig), the weight hourly space velocity (WHSV) in said primary reaction zone is in the range from about 0.5 to about 20 hr$^{-1}$, and said catalyst therein has an activity, alpha, in the range from 1 to about 20, to provide a per pass conversion of at least 70% olefins in said feedstock to said intermediate range olefins, and a pentane to pentene ratio ($C_5$: $C_5^=$) in said primary effluent of less than 0.2:1; and, said primary effluent is substantially free of aromatics.

3. The process of claim 2 wherein said secondary reaction zone operates in a distillate mode at a pressure higher than that of said primary reaction zone, including,
   (i) separating a substantially $C_{10}^+$ stream from said primary effluent, and,
   (ii) contacting a substantially $C_{10}^+$-free stream with said oligomerization catalyst in said secondary reaction zone under oligomerization conditions with at least 50% conversion of olefins in said intermediate stream.

4. The process of claim 3 wherein said primary and secondary reaction zones operate with recycle of oligomerizable components to produce more distillate product than gasoline.

5. The process of claim 2 wherein said secondary reaction zone operates in a lubes mode at a pressure higher than that of said primary zone, to provide at least 55% conversion of olefins in said intermediate stream.

6. The process of claim 3, including,
   (i) partially condensing said primary effluent by cooling it to a temperature in the range from about 93° C. (200° F.) to about 260° C. (500° F.) to produce a "wild" $C_{10}^+$ liquid condensate,
   (ii) separating said wild $C_{10}^+$ liquid from $C_9^-$ vapors in said primary effluent in a liquid-gas separating zone,
   (iii) selectively flowing a portion, or none, of said wild $C_{10}^+$ liquid condensate to a second fractionation zone for separating gasoline and distillate,
   (iv) flowing said $C_9^-$ vapors from said liquid-gas separating zone to a first fractionation zone, and,
   (v) withdrawing from said first fractionation zone, said $C_5$–$C_9$ intermediate stream substantially free of $C_{10}^+$ hydrocarbons for feed to said secondary reaction zone.

7. The process of claim 3 operating in a distillate mode, including,
   (i) partially condensing said primary effluent by cooling to a temperature sufficient to separate said $C_5^+$ hydrocarbons from said $C_4^-$ hydrocarbons,
   (ii) separating said $C_5^+$ hydrocarbons from said $C_4^-$ hydrocarbons in a first separation zone,
   (iii) flowing said $C_5^+$ hydrocarbons to a second fractionation zone for separating gasoline and distillate,
   (iv) recovering a $C_5$–$C_9$ gasoline range stream substantially free of $C_{10}^+$ hydrocarbons from said second separation zone, and,
   (v) feeding said $C_5$–$C_9$ gasoline range stream to said secondary reaction zone.

8. The process of claim 5 including,
operating said secondary reaction zone with a fixed bed of said oligomerization catalyst within which all hydrocarbons are at pressure above about 3200 kPa (450 psig) and a temperature in the range from about 204° C.–343° C. (400° F.–650° F.).

9. The process of claim 1 wherein said secondary reaction zone operates with a fluid bed of catalyst within which all hydrocarbons are at near-critical or super-critical pressure and temperature conditions sufficiently high to keep all hydrocarbons in the super-dense phase and to ensure that no liquid phase is present therein.

10. The process of claim 4 wherein said secondary reaction zone operates with a fluid bed of catalyst within which all hydrocarbons are at near-critical or super-critical pressure and temperature conditions sufficiently high to keep all hydrocarbons in the super-dense phase and to ensure that no liquid phase is present therein.

11. A multistage catalytic process for converting a FCC gas, light gas or light naphtha feedstock containing at least 10% by weight olefins, to a product rich in $C_{10}^+$ aliphatic hydrocarbons, comprising,
  (a) maintaining a primary reaction zone containing a bed of zeolite catalyst particles at oligomerization pressure and temperature for said olefins,
  (b) passing hot feedstock vapor upwardly through said bed in a single pass at reaction severity conditions sufficient to upgrade said olefins to intermediate range olefins mainly in the $C_5$–$C_9$ range, with a per pass conversion of at least 70%, and a pentane to pentane ratio ($C_5:C_5^=$) of less than 0.2:1,
  (c) recovering from said primary reaction zone a primary effluent containing olefins with a major amount of $C_5^+$ olefinic hydrocarbons including at least 1 part by weight of distillate per 10 parts of gasoline, less than about 3 mol % aromatics, and a minor amount of $C_4^-$ olefinic hydrocarbons,
  (d) removing substantially all said $C_4^-$ hydrocarbons from said primary effluent to provide a substantially olefinic $C_5^+$ intermediate stream,
  (e) further oligomerizing said intermediate stream in a secondary reaction zone by contacting said intermediate stream with a medium pore shape selective acid oligomerization catalyst under oligomerization conditions in the absence of added hydrogen to produce a predominantly $C_{10}^+$ secondary effluent, at a per pass conversion of at least 50% of olefins therein, and,
  (f) recovering a $C_{10}^+$ aliphatic product stream from said secondary effluent.

12. The process of claim 11 wherein a portion of said secondary effluent is recycled to said primary reaction zone.

13. The process of claim 11 wherein said bed is a fluidized bed, said catalyst in said primary reaction zone has an equilibrated activity, alpha, in the range from about 1 to about 20, said fluidized bed operates at a WHSV in the range from about 0.1 to about 20 $hr^{-1}$, said particles are in the size range from about 1 to about 150 microns, having an average catalyst particle size in the range from about 20 to 100 microns, and, contain about 10 to 25% by weight of fine particles having a particle size less than 32 microns.

14. The process of claim 13 including withdrawing a portion of coked catalyst from said primary reaction zone, oxidatively regenerating said coked catalyst, and returning regenerated catalyst to said primary reaction zone at a predetermined rate sufficient to maintain activity of the catalyst such that the weight ratio of $C_3$–$C_5$ alkanes:alkenes in said primary effluent is in the range from about 0.04:1 to about 0.2:1 under conditions of reaction severity to effect feedstock conversion.

15. The process of claim 14 wherein
  (i) said fluidized bed contains particles comprising about 5 to 95% by weight of ZSM-5 or zeolite beta metallosilicate zeolite having a crystal size in the range from about 0.02 to 2 microns,
  (ii) said secondary reaction zone operates in a distillate mode as a fixed bed at a pressure higher than that of said primary reaction zone, under conditions which produce at least 50% conversion of olefins in said intermediate stream, and,
  (iii) operation of said secondary reaction zone is periodically interrupted to permit regeneration of catalyst in said secondary reaction zone.

16. The process of claim 15 including,
  (i) separating a substantially $C_{10}^+$ stream from said primary effluent, and,
  (ii) contacting a substantially $C_{10}^+$-free stream with said oligomerization catalyst to provide a net distillate yield which is higher than the net gasoline yield.

17. The process of claim 14 wherein
  (i) said fluidized bed contains particles comprising about 5 to 95% by weight of zeolite beta or ZSM-5 metallosilicate zeolite having a crystal size in the range from about 0.02 to 2 microns,
  (ii) said secondary reaction zone operates in a distillate mode as a fluid bed at a pressure higher than that of said primary reaction zone within which all hydrocarbons are at near-critical or super-critical pressure and temperature conditions sufficiently high to keep said hydrocarbons in the super-dense phase and to ensure that no liquid phase is present therein, so as to produce a net distillate yield which is higher than the net gasoline yield and,
  (iii) operation of said secondary reaction zone is essentially continuous.

18. The process of claim 14 wherein said secondary reaction zone operates in a lubes mode at a pressure higher than that of said primary reaction zone, and, with at least 55% conversion of olefins in said intermediate stream.

19. A multistage catalytic process for converting lower olefinic feedstock to a $C_{10}^+$ distillate product, comprising,
  (a) contacting $C_3$–$C_4$-rich feedstock having an alkene content of at least 10% by weight, at elevated temperature in a continuous primary reaction zone with a first shape selective medium pore zeolite oligomerization catalyst to convert at least 80% of propene to $C_5^+$ olefinic hydrocarbons under reaction severity conditions sufficient to produce pentane and pentene in a weight ratio of about 0.05 to 2:1, said first shape selective catalyst having an average equilibrated alpha in the range from about 0.1 to about 20,
  (b) cooling effluent from said primary reaction zone to condense at least a portion thereof and flowing it to a debutanizing zone in which gaseous $C_4^-$ components are separated from $C_5^+$ components,
  (c) flowing an intermediate stream of said $C_5^+$ components to a fractionation zone located upstream of a secondary reaction zone and separating substantially $C_5$–$C_9$ gasoline from $C_{10}^+$ distillate so as to recover a substantially $C_{10}^+$-free gasoline stream,
  (d) contacting said substantially $C_{10}^+$-free gasoline stream with a second shape selective medium pore zeolite oligomerization catalyst having an acid cracking activity of at least 5, maintained in said secondary reaction zone under higher pressure than said primary reaction zone, to produce a secondary effluent in which at least 50% of said olefins in said intermediate stream are converted per pass to $C_{10}^+$ components,
  (e) at least partially condensing said secondary effluent to condense substantially all said $C_{10}^+$ components in a gas-liquid separation zone from which gaseous $C_9^-$ components are recycled to said primary reaction zone,
  (f) flowing said $C_{10}^+$ components from said second gas-liquid separation zone to said fractionation zone for separating gasoline and distillate, and,
  (g) recovering said $C_{10}^+$ distillate product.

20. The process of claim 19 wherein (i) said primary reaction zone operates at moderate pressure below 2170 kPa (300 psig), an alpha in the range from 1 to 10, the weight hourly space velocity WHSV in said primary reaction zone is in the range from about 0.5 to about 20 hr$^{-1}$, with an inlet temperature in the range from about 38° C. (100° F.) to about 260° C. (500° F.), and an outlet temperature in the range from about 260° C. (500° F.) to about 371° C. (700° F.), to provide a per pass conversion of at least 70% olefins in said feedstock to said intermediate range olefins, and, (ii) said secondary reaction zone operates with catalyst having an average activity alpha greater than 10, at weight hourly space velocity WHSV in the range from about 0.1 to about 10 hr$^{-1}$, at an inlet pressure in excess of about 3200 kPa (450 psig), an inlet temperature in the range from about 149° C. (300° F.) to about 232° C. (450° F.), an outlet temperature in the range from about 232° C. (450° F.) to about 343° C. (650° F.).

21. A multistage catalytic process for converting lower olefinic feedstock to a $C_{10}{}^+$ distillate product, comprising, (a) contacting $C_3$–$C_4$-rich feedstock having an alkene content of at least 10% by weight, at elevated temperature in a continuous primary reaction zone with a first shape selective medium pore zeolite oligomerization catalyst to convert at least 80% of propene to $C_5{}^+$ olefinic hydrocarbons under reaction severity conditions sufficient to produce pentane and pentene in a weight ratio of about 0.05:1 to 2:1, said first shape selective catalyst having an average equilibrated alpha in the range from about 1 to about 20, (b) cooling effluent from said primary reaction zone to condense at least a portion of said hydrocarbons in a first gas-liquid separation zone in which gaseous $C_9{}^-$ components are separated from a "wild" $C_{10}{}^+$ liquid stream, (c) flowing said $C_9{}^-$ components to a first fractionation zone and separating a substantially $C_5$–$C_9$ gasoline from light $C_4{}^-$ hydrocarbons so as to recover a substantially $C_{10}{}^+$-free gasoline stream, (d) contacting said substantially $C_{10}{}^+$-free gasoline stream with a second shape selective medium pore zeolite oligomerization catalyst having an acid cracking activity of at least 5, maintained in a higher pressure secondary reaction zone than said primary reaction zone, to produce a secondary effluent from which is recovered a higher net yield of $C_{10}{}^+$ components that net yield of gasoline, (e) cooling said secondary effluent to condense substantially all said $C_{10}{}^+$ components in a second gas-liquid separation zone from which gaseous $C_9{}^-$ components are recycled to said primary reaction zone, (f) flowing said $C_{10}{}^+$ components from said second gas-liquid separation zone to a second fractionation zone for separating gasoline and distillate, said second fractionation zone being located downstream of said secondary reaction zone, (g) flowing from 0 to 100% of said wild liquid stream to said second fractionation zone for separating gasoline and distillate, second fractionation zone, and, (h) recovering said $C_{10}{}^+$ distillate product.

22. The process of claim 21 wherein said first shape selective catalyst is zeolite beta.

23. The process of claim 22 wherein (i) said primary reaction zone operates at moderate pressure below 2170 kPa (300 psig), an alpha in the range from 1 to 10, the weight hourly space velocity WHSV in said primary reaction zone is in the range from about 0.5 to about 20 hr$^{-1}$, with an inlet pressure in the range from about 150 psig to about 250 psig, an inlet temperature in the range from about (100° F.) to about (500° F.) and an outlet temperature in the range from about 650° F. to about 750° F., to provide a per pass conversion of at least 70% olefins in said feedstock to said intermediate range olefins, and, (ii) said secondary reaction zone operates with catalyst having an average activity alpha greater than 10, at weight hourly space velocity WVSV in the range from about 0.1 to about 10 hr$^{-1}$, at an inlet pressure in excess of about 3200 kPa (450 psig), an inlet temperature in the range from about 149° C. (300° F.) to about 204° C. (400° F.), and, an outlet temperature in the range from about 260° C. (500° F.) to about 343° C. (650° F.).

24. The process of claim 22 operating in a first distillate mode, comprising, (a) debutanizing the effluent from said primary reaction zone;

(b) feeding a debutanized $C_5{}^+$ stream to a second separation zone to separate mainly gasoline and lighter $C_{10}{}^-$ components for feed to said secondary reaction zone;

(c) oligomerizing separated $C_{10}{}^-$ components in said secondary reaction zone to provide therefrom a secondary effluent containing more distillate than gasoline, (d) cooling said secondary effluent and flowing it to said second separation zone; and, (e) recovering the bottoms from the said secondary separation zone as distillate product.

25. The process of claim 22 operating in a second distillate mode, comprising, (a) condensing at least a portion of effluent from said primary reaction zone so as to separate a "wild $C_{10}$" portion from gaseous, mainly $C_{10}{}^-$ hydrocarbons in a first high pressure and high temperature separating (first HTS) means, said "wild $C_{10}$" portion being separated as a HTS liquid phase;

(b) debutanizing said mainly $C_{10}{}^-$ hydrocarbons in a first, relatively low temperature fractionation zone to obtain an intermediate stream substantially free of $C_{10}{}^+$ hydrocarbons;

(c) feeding said intermediate stream substantially free of $C_{10}{}^+$ hydrocarbons to said secondary reaction zone;

(d) oligomerizing said intermediate stream substantially free of $C_{10}{}^+$ hydrocarbons in said secondary reaction zone to provide a secondary effluent in which the per pass conversion of olefins in said intermediate stream to $C_{10}{}^+$ hydrocarbons is at least 50%;

(e) flowing said secondary effluent and HTS liquid phase to a second HTS or second debutanizing zone;

(f) mixing $C_{10}{}^-$ hydrocarbons separated in either said second HTS, or second debutanizing zone, with said primary effluent or said intermediate stream substantially free of $C_{10}{}^+$ hydrocarbons;

(g) mixing the liquid phase from the second HTS, or the bottoms of the second debutanizer, with said "wild $C_{10}$" portion, to form a predominantly distillate-containing stream; and, (h) flowing the distillate-containing stream to a second, relatively high temperature fractionation zone to recover product distillate.

26. The process of claim 22 wherein, said first separation zone is a first fractionation zone operating with an inlet pressure in the range from about 140–240 psig, and inlet temperature in the range from about 200°–300° F. to debutanize cooled effluent from said primary reaction zone; and, said $C_{10}^+$ product is recovered from a second separation zone.

27. The process of claim 26 wherein, said second separation zone is a second fractionation zone operating with an inlet pressure in the range from about 0–40 psig, and inlet temperature in the range from about 300°–400° F., to separate gasoline range hydrocarbons from $C_{10}^+$ product.

28. The process of claim 21 wherein said secondary reaction zone operates in a lubes mode at a pressure higher than that of said primary reaction zone, and, with at least 55% conversion of olefins in said intermediate stream.

29. The process of claim 28 including, operating said secondary reaction zone with a fixed bed of said oligomerization catalyst within which all hydrocarbons are at a pressure above about 3200 kPa (450 psig) and a temperature in the range from about 204° C.–343° C. (400° F.–650° F.).

30. The process of claim 21 wherein said secondary reaction zone operates with a fluid bed of catalyst within which all hydrocarbons are at near-critical or super-critical pressure and temperature conditions sufficiently high to keep all hydrocarbons in the super-dense phase and to ensure that no liquid phase is present therein.

* * * * *

UNITED STATES PATENT AND TRADEMARK OFFICE
CERTIFICATE OF CORRECTION

PATENT NO. : 4,855,524

DATED : August 8, 1989

INVENTOR(S) : M. N. Harandi & H. Owen

It is certified that error appears in the above-identified patent and that said Letters Patent is hereby corrected as shown below:

Column 4, line 11, add "MOG" after the words "first stage"

Column 13, line 39, add the word "reactor" after "MOG"

Signed and Sealed this

Twenty-second Day of October, 1991

*Attest:*

HARRY F. MANBECK, JR.

*Attesting Officer*  *Commissioner of Patents and Trademarks*